(12) United States Patent
Eckelberry et al.

(10) Patent No.: US 9,085,745 B2
(45) Date of Patent: Jul. 21, 2015

(54) SYSTEMS AND METHODS FOR EXTRACTING NON-POLAR LIPIDS FROM AN AQUEOUS ALGAE SLURRY AND LIPIDS PRODUCED THEREFROM

(75) Inventors: Nicholas Eckelberry, Los Angeles, CA (US); Michael Phillip Green, Pacheco, CA (US); Scott Alexander Fraser, Manhattan Beach, CA (US)

(73) Assignee: OriginOil, Inc., Los Angeles, CA (US)

( * ) Notice: Subject to any disclaimer, the term of this patent is extended or adjusted under 35 U.S.C. 154(b) by 109 days.

(21) Appl. No.: 13/642,096

(22) PCT Filed: Oct. 19, 2010

(86) PCT No.: PCT/US2010/053260
§ 371 (c)(1),
(2), (4) Date: Feb. 1, 2013

(87) PCT Pub. No.: WO2011/133181
PCT Pub. Date: Oct. 27, 2011

(65) Prior Publication Data
US 2013/0211113 A1    Aug. 15, 2013

(51) Int. Cl.
*C11B 1/00* (2006.01)
*B01D 57/00* (2006.01)
(Continued)

(52) U.S. Cl.
CPC . *C11B 3/005* (2013.01); *A23D 9/02* (2013.01); *C11B 1/10* (2013.01); *C12M 47/06* (2013.01); *C12N 1/066* (2013.01); *C12N 13/00* (2013.01)

(58) Field of Classification Search
CPC ............ C11B 1/12; C11B 1/00; C11B 1/104; C11B 1/02; B01D 11/0203; B01D 57/02; F04B 19/006; B01L 2300/0816; B01L 2400/0415; B01L 3/50273; G01N 27/44704; G01N 27/44747; G01N 27/44791; G01N 27/44743; G01N 27/44752; G01N 27/44769
USPC ................. 554/8; 204/450, 451, 600, 601
See application file for complete search history.

(56) References Cited

U.S. PATENT DOCUMENTS

| | | |
|---|---|---|
| 1,740,659 A | 12/1929 | MacDonald |
| 1,988,932 A | 1/1935 | Arnold |

(Continued)

FOREIGN PATENT DOCUMENTS

| | | |
|---|---|---|
| EP | 1277831 A2 | 1/2003 |
| GB | 2477277 A | 8/2011 |

(Continued)

OTHER PUBLICATIONS

Liam Brenan, Biofuels from Microalgae: A review of technologies for production, processing and extractions of biofuels and co-products, Renewable and Sustainable Energy Reviews. Feb. 2010, vol. 14, No. 2, pp. 557-577, ISSN 1364-0321.

(Continued)

*Primary Examiner* — Deborah D Carr
(74) *Attorney, Agent, or Firm* — Jarod R. Marrott; Kirton | McConkie

(57) ABSTRACT

Methods, systems, and apparatuses for extracting non-polar lipids from microalgae are achieved using a lipid extraction device having an anode and a cathode that forms a channel and defines a fluid flow path through which an aqueous slurry is passed. An electromotive force is applied across the channel at a gap distance in a range from 0.5 mm to 200 mm to cause the non-polar lipids to be released from the algae cells. The non-polar lipids can be extracted at a high throughput rate and with low concentrations of polar lipids such as phospholipids and chlorophyll.

18 Claims, 18 Drawing Sheets

(51) Int. Cl.
*B01D 57/02* (2006.01)
*C02F 1/40* (2006.01)
*C11B 3/00* (2006.01)
*A23D 9/02* (2006.01)
*C11B 1/10* (2006.01)
*C12M 1/00* (2006.01)
*C12N 1/06* (2006.01)
*C12N 13/00* (2006.01)

(56) References Cited

U.S. PATENT DOCUMENTS

| | | |
|---|---|---|
| 3,198,119 A | 8/1965 | Mead |
| 3,315,270 A | 4/1967 | Hersch |
| 3,409,530 A | 11/1968 | Locke et al. |
| 3,479,873 A | 11/1969 | Hermanns |
| 3,752,747 A | 8/1973 | Treharne et al. |
| 3,985,634 A | 10/1976 | Larson et al. |
| 4,039,422 A | 8/1977 | Packer |
| 4,169,033 A | 9/1979 | Dunagan |
| 4,243,751 A | 1/1981 | Swartz |
| 4,253,271 A | 3/1981 | Raymond |
| 4,269,690 A | 5/1981 | Graham, III |
| 4,437,954 A | 3/1984 | Sammells et al. |
| 4,458,524 A | 7/1984 | Meador et al. |
| 4,681,116 A | 7/1987 | Settler |
| 4,752,740 A | 6/1988 | Steininger |
| 4,981,582 A | 1/1991 | Yoon et al. |
| 5,128,304 A | 7/1992 | Ito |
| 5,511,408 A | 4/1996 | Yoshioka et al. |
| 5,543,034 A | 8/1996 | Hilbertz |
| 5,614,378 A | 3/1997 | Yang et al. |
| 5,783,052 A | 7/1998 | Bakhir et al. |
| 5,804,384 A | 9/1998 | Muller et al. |
| 5,858,199 A | 1/1999 | Hanak |
| 5,866,910 A | 2/1999 | Cooke et al. |
| 5,951,875 A | 9/1999 | Kanel et al. |
| 6,269,261 B1 | 7/2001 | Ootomo |
| 6,279,611 B2 | 8/2001 | Uematsu et al. |
| 6,391,619 B1 | 5/2002 | Cheung |
| 6,709,560 B2 | 3/2004 | Andelman et al. |
| 6,912,895 B1 | 7/2005 | Jaeger |
| 6,942,767 B1 | 9/2005 | Fazzina et al. |
| 7,136,699 B2 | 11/2006 | Palti |
| 7,420,658 B2 | 9/2008 | Petterson et al. |
| 7,510,864 B2 | 3/2009 | Krichevsky et al. |
| 7,790,427 B1 | 9/2010 | Chauhan et al. |
| 7,824,904 B1 | 11/2010 | Dimanshteyn |
| 8,003,379 B2 | 8/2011 | Goldman et al. |
| 8,105,474 B2 | 1/2012 | Fan |
| 2001/0011457 A1 | 8/2001 | Shishido et al. |
| 2002/0079270 A1 | 6/2002 | Borodyanski et al. |
| 2002/0123126 A1 | 9/2002 | Cheun et al. |
| 2003/0113832 A1 | 6/2003 | Lauf |
| 2004/0067574 A1* | 4/2004 | Bijl et al. .................. 435/252.3 |
| 2004/0096943 A1 | 5/2004 | Marx et al. |
| 2005/0170479 A1* | 8/2005 | Weaver et al. ................. 435/134 |
| 2006/0141615 A1 | 6/2006 | Lu |
| 2006/0163056 A1 | 7/2006 | Grebenyuk et al. |
| 2006/0172417 A1 | 8/2006 | Rathenow et al. |
| 2006/0240544 A1 | 10/2006 | Shiau |
| 2007/0056842 A1 | 3/2007 | Roychowdhury |
| 2008/0160593 A1* | 7/2008 | Oyler ............................ 435/166 |
| 2009/0029445 A1 | 1/2009 | Eckelberry |
| 2009/0047722 A1 | 2/2009 | Wilkerson et al. |
| 2009/0087900 A1 | 4/2009 | Davey et al. |
| 2009/0104594 A1 | 4/2009 | Webb |
| 2009/0105965 A1 | 4/2009 | Birk et al. |
| 2009/0127128 A1 | 5/2009 | Kitaori et al. |
| 2010/0050502 A1 | 3/2010 | Wu et al. |
| 2010/0081835 A1 | 4/2010 | Wu et al. |
| 2010/0120095 A1 | 5/2010 | Stro azzo-Mougin et al. |
| 2010/0151540 A1 | 6/2010 | Gordon et al. |
| 2010/0170151 A1 | 7/2010 | Huber |
| 2010/0233761 A1 | 9/2010 | Czartoski |
| 2011/0095225 A1 | 4/2011 | Eckelberry et al. |
| 2011/0107655 A1 | 5/2011 | Kempkes et al. |
| 2011/0308962 A1 | 12/2011 | Eckelberry et al. |
| 2012/0021481 A1 | 1/2012 | Hebner et al. |
| 2012/0094366 A1 | 4/2012 | Ludwig |
| 2012/0129244 A1 | 5/2012 | Green et al. |

FOREIGN PATENT DOCUMENTS

| | | |
|---|---|---|
| KR | 10873700 B1 * | 12/2008 |
| KR | 100873700 B1 | 12/2008 |
| KR | 1020090025221 A | 3/2009 |
| KR | 1020090025221 A1 * | 3/2009 |
| WO | 9420420 | 9/1994 |
| WO | 2008098298 | 9/2008 |
| WO | 2009017677 A2 | 2/2009 |
| WO | 2009029445 A1 | 6/2009 |
| WO | 2009154437 A1 | 12/2009 |
| WO | 2010123903 A1 | 10/2010 |
| WO | 2012129031 A2 | 9/2012 |

OTHER PUBLICATIONS

OriginOil, 'OriginOil Announces Breakthrough Innovation to Increase Algae Yield'[online], Mar. 21, 2011 [retrieved on Jan. 29, 2013]. htttp://files.shareholder.com/downloads/AMDA-LWSGL/0x0x529755/e09aa652-7590-415c-b7ef-5a4961e2d2b9/OOIL__News__2011__3__21__General__Releases.pdf; p. 1.

Johnson, More Algae Action: OriginOil Plans to 'Milk' Algae for Oil, Wall Street Journal, Jul. 28, 2009, blogs.wsj.com/environmentalcapital/2009/07/28/more-algae.

Carey; et al. (2004) Marx generator design and performance, Power Modular Symposium, 2002 and 2002 High-Voltage Workshop. Conference Record of the Twenty-Fifth International, Jun. 30-Jul. 3, 2002.

Mehta, R. & Hawxby, K. Proc. Okla. Acad. Sci. (1977) vol. 57, pp. 54-60.

* cited by examiner

| Test | Sample # | Time | Control Sample Details | | | | | | Flow Rate | EMP | | Extraction Details | | |
|---|---|---|---|---|---|---|---|---|---|---|---|---|---|---|
| | | | Seed Date | pH | Cond. (mS/cm) | Dry Mass Conc. (mg/L) | Lipid Content mg/L | % of dry | °C | | V | A | Ext. Eff. | Notes |
| 1 | 20090812-2 | | N/A | 7.1 | 8.82 | 433 | 23.85k3 | 5 | | 0.26 | 4.3 | 22 | 90% | 6" EMP cell |
| 2 | 20090813-2 | | N/A | 6.8 | 9.31 | 207 | 26.91 | 13 | | 0.26 | 3.4 | 20 | 88% | 6" EMP cell |
| 3 | 20090813-3 | | N/A | 6.8 | 9.31 | 207 | 26.91 | 13 | | 0.26 | 3.4 | 20 | 95% | 6" EMP cell |
| 4 | | | 9/11/09 | 7.1 | 8.99 | 410 | 33.62 | 8 | | 0.40 | 12.4 | 18 | 91% | 6" EMP cell |
| 5 | 20091007-3 | | 9/02/09 | 7.5 | 8.15 | 800 | 159.2 | 20 | | 0.20 | 4.8 | 20 | 12% | 12" EMP cell |
| 6 | 20091007-3 | | 9/11/09 | 7.5 | 8.18 | 500 | 80.75 | 16 | | 0.30 | 4.7 | 20 | 52% | 12" EMP cell |
| 7 | 20091020-2 | | 9/11/09 | 7.8 | 7.89 | 210 | 50.4 | 24 | | 0.25 | 12.1 | 5 | 69% | 6" EMP cell |
| 7 | 20091020-5 | | 9/11/09 | 7.8 | 7.89 | 210 | 50.4 | 24 | | 0.25 | 11.9 | 10 | 72% | 6" EMP cell |
| 7 | 20091020-8 | | 9/11/09 | 7.8 | 7.89 | 210 | 50.4 | 24 | | 0.25 | 11.8 | 15 | 97% | 6" EMP cell |
| 7 | 20091020-10 | | 9/11/09 | 7.8 | 7.89 | 210 | 50.4 | 24 | | 0.25 | 11.6 | 20 | 90% | 6" EMP cell |
| 7 | 20091020-14 | | 9/11/09 | 7.8 | 7.89 | 210 | 50.4 | 24 | | 0.38 | 12.1 | 5 | 52% | 6" EMP cell |
| 7 | 20091020-17 | | 9/11/09 | 7.8 | 7.89 | 210 | 50.4 | 24 | | 0.38 | 11.9 | 10 | 78% | 6" EMP cell |
| 7 | 20091020-20 | | 9/11/09 | 7.8 | 7.89 | 210 | 50.4 | 24 | | 0.38 | 11.8 | 15 | 71% | 6" EMP cell |
| 7 | 20091020-23 | | 9/11/09 | 7.8 | 7.89 | 210 | 50.4 | 24 | | 0.38 | 11.6 | 20 | 78% | 6" EMP cell |
| 7 | 20091020-26 | | 9/11/09 | 7.8 | 7.89 | 210 | 50.4 | 24 | | 0.50 | 12.1 | 5 | 57% | 6" EMP cell |
| 7 | 20091020-29 | | 9/11/09 | 7.8 | 7.89 | 210 | 50.4 | 24 | | 0.50 | 11.9 | 10 | 55% | 6" EMP cell |
| 7 | 20091020-32 | | 9/11/09 | 7.8 | 7.89 | 210 | 50.4 | 24 | | 0.50 | 11.8 | 15 | 52% | 6" EMP cell |
| 7 | 20091020-35 | | 9/11/09 | 7.8 | 7.89 | 210 | 50.4 | 24 | | 0.50 | 11.6 | 20 | 45% | 6" EMP cell |
| 8 | 0.3 | | 9/11/09 | 7.3 | 7.93 | 320 | 57.6 | 18 | | 0.25 | 5.3 | 20 | 83% | 6" EMP cell |
| 8 | 0.4 | | 9/11/09 | 7.3 | 7.93 | 320 | 57.6 | 18 | | 0.25 | 5.3 | 20 | 81% | 6" EMP cell |
| 8 | 0.5 | | 9/11/09 | 7.3 | 7.93 | 320 | 57.6 | 18 | | 0.25 | 5.3 | 20 | 96% | 6" EMP cell |
| 9 | 1130-3 | | 10/19/09 | 7.5 | 8.15 | 320 | 55.0 | 18 | | 0.25 | 3.7 | 15 | 72% | 6" EMP cell |
| 9 | 1130-4 | | 10/19/09 | 7.5 | 8.15 | 320 | 55.0 | 18 | | 0.25 | 4.0 | 20 | 80% | 6" EMP cell |
| 9 | 1130-8,9 | | 10/19/09 | 7.5 | 8.15 | 320 | 55.0 | 18 | | 0.38 | 4.0 | 20 | 77% | 6" EMP cell |
| 9 | 1130-12 | | 10/19/09 | 7.5 | 8.15 | 320 | 55.0 | 18 | | 0.38 | 3.7 | 15 | 93% | 6" EMP cell |
| | | | | | | | | | | | | | Lipid Analysis by CSULB | |
| 10 | 20091220-13,14 | | 12/16/09 | 7.7 | 7.42 | 280 | 59.0 | 21 | | 0.25 | 2.1 | 5 | ** | PEMP with Heat+MX; Biomass sank after 60 min |
| 10 | 20091220-17,18 | | 12/16/09 | 7.7 | 7.42 | 280 | 59.0 | 21 | | 0.25 | 3.1 | 10 | | PEMP with Heat+MX; Biomass sank after 25 min |
| 10 | 20091220-19,20 | | 12/16/09 | 7.7 | 7.42 | 280 | 59.0 | 21 | | 0.25 | 2.6 | 15 | 65% | PEMP with Heat+MX; Biomass sank instantly |
| 10 | 20091220-27,28 | | 12/16/09 | 7.7 | 7.42 | 280 | 59.0 | 21 | | 0.25 | 3.8 | 20 | | PEMP with Heat+MX; Biomass sank instantly |
| 10 | 20091220-15,16 | | 12/16/09 | 7.7 | 7.42 | 280 | 59.0 | 21 | | 0.50 | 2.1 | 5 | | PEMP with Heat+MX; All biomass floated |

Fig. 16

| Test | Sample # | Time | Control Sample Details |||||| Flow Rate | EMP || Extraction Details ||
|---|---|---|---|---|---|---|---|---|---|---|---|---|---|
| | | | Seed Date | pH | Cond. (mS/cm) | Dry Mass Conc. (mg/L) | Lipid Content ||°C| | V | A | Ext. Eff. | Notes |
| | | | | | | | mg/L | % of dry | | | | | | |
| 10 | 20091220-21,22 | | 12/16/09 | 7.7 | 7.42 | 280 | 59.0 | 21 | | 0.50 | 2.6 | 15 | 55% | PEMP with Heat+MX | All biomass floated |
| 10 | 20091220-29,30 | | 12/17/09 | 7.7 | 7.42 | 280 | 59.0 | 21 | | 0.50 | 3.8 | 20 | | PEMP with Heat+MX | Biomass sank slowly (1 day) |
| 10 | 20091220-23,24 | | 12/17/09 | 7.7 | 7.42 | 280 | 59.0 | 21 | | 1.00 | 2.6 | 15 | | PEMP with Heat+MX | All biomass floated |
| 10 | 20091220-25,26 | | 12/17/09 | 7.7 | 7.42 | 280 | 59.0 | 21 | | 2.00 | 2.6 | 15 | | PEMP with Heat+MX | All biomass floated |
| 10 | 20091220-1,2 | | 12/17/09 | 7.7 | 7.42 | 280 | 59.0 | 21 | | 0.50 | 3.5 | 15 | 95% | SSE No MX/No Heat | Biomass was suspended |
| 10 | 20091220-5,6 | | 12/17/09 | 7.7 | 7.42 | 280 | 59.0 | 21 | | 0.50 | 2.5 | 15 | 107% | Pipe SSE No MX/Heat | All biomass floated |
| 10 | 20091220-9,10 | | 12/17/09 | 7.7 | 7.42 | 280 | 59.0 | 21 | | 0.50 | 3.6 | 15 | 50% | Pipe SSE MX/No Heat | Biomass was suspended |
| 10 | 20091220-3,4 | | 12/18/09 | 7.7 | 7.42 | 280 | 59.0 | 21 | | 1.00 | 3.5 | 15 | | PSSE No MX/Heat | Biomass was suspended |
| 10 | 20091220-7,8 | | 12/18/09 | 7.7 | 7.42 | 280 | 59.0 | 21 | | 1.00 | 2.5 | 15 | | Pipe SSE No MX/Heat | All biomass floated |
| 10 | 20091220-11,12 | | 12/18/09 | 7.7 | 7.42 | 280 | 59.0 | 21 | | 1.00 | 3.6 | 15 | | Pipe SSE MX/No Heat | Biomass was suspended |
| 11 | 20100104-11 | 3:00 PM | 12/29/09 | 8.4 | 7.99 | 285 | 19 | 7 | 22 | 0.25 | 3.5 | 12 | 45% | 6" EMP, No MX/Heat | |
| 11 | 20100104-12 | 3:00 PM | 12/29/09 | 8.4 | 7.99 | 285 | 19 | 7 | 22 | 0.25 | 3.7 | 14 | 31% | 6" EMP, No MX/Heat | |
| 11 | 20100104-13 | 3:00 PM | 12/29/09 | 8.4 | 7.99 | 285 | 19 | 7 | 22 | 0.25 | 3.7 | 15 | 39% | 6" EMP, No MX/Heat | |
| 11 | 20100104-14 | 3:00 PM | 12/29/09 | 8.4 | 7.99 | 285 | 19 | 7 | 22 | 0.25 | 4 | 20 | 41% | 6" EMP, No MX/Heat | |
| 11 | 20100104-15 | 3:00 PM | 12/29/09 | 8.4 | 7.99 | 285 | 19 | 7 | 22 | 0.25 | 3.9 | 19 | 98% | 6" EMP, No MX/Heat | Lipid Analysis by CSULB |
| 11 | 20100104-16 | 3:00 PM | 12/29/09 | 8.4 | 7.99 | 285 | 19 | 7 | 22 | 0.50 | 3.9 | 20 | 67% | 6" EMP, No MX/Heat | |
| 11 | 20100104-17 | 3:00 PM | 12/29/09 | 8.4 | 7.99 | 285 | 19 | 7 | 22 | 0.50 | 3.8 | 18 | 96% | 6" EMP, No MX/Heat | |
| 11 | 20100104-18 | 3:00 PM | 12/29/09 | 8.4 | 7.99 | 285 | 19 | 7 | 22 | 0.50 | 3.7 | 15 | 69% | 6" EMP, No MX/Heat | |
| 12 | 1,2 | 1:00 PM | 1/07/10 | 7.4 | 7.64 | 255 | 38.57 | 15 | | 0.50 | 7 | 15 | 16% | Pipe SSE, MX | In-house analyzed |
| 12 | 3,4 | 1:00 PM | 1/07/10 | 7.4 | 7.64 | 255 | 38.57 | 15 | | 0.25 | 7 | 15 | 19% | Pipe SSE, Heat | |
| 12 | 5,6 | 1:00 PM | 1/07/10 | 7.4 | 7.64 | 255 | 38.57 | 15 | | 0.50 | 7 | 15 | 23% | Pipe SSE, Heat | |

*Fig. 16 (Continued)*

| Test | Sample # | Time | Control Sample Details | | | | | | | Flow Rate | EMP | | Extraction Details | | |
|---|---|---|---|---|---|---|---|---|---|---|---|---|---|---|---|
| | | | Seed Date | pH | Cond. (mS/cm) | Dry Mass Conc. (mg/L) | Lipid Content mg/L | Lipid Content % of dry | °C | | V | A | Ext. Eff. | Notes | |
| 12 | 7,8 | 1:00 PM | 1/07/10 | 7.4 | 7.64 | 255 | 38.57 | 15 | | 0.50 | 7 | 15 | 45% | PSSE, No MX/Heat | |
| 12 | 11,12 | 1:00 PM | 1/07/10 | 7.4 | 7.64 | 255 | 38.57 | 15 | | 1.00 | 7 | 12 | 21% | Pipe SSE, MX+Heat | In-house analyzed |
| 12 | 13,14 | 1:00 PM | 1/07/10 | 7.4 | 7.64 | 255 | 38.57 | 15 | | 0.50 | 7 | 15 | 24% | Pipe SSE, MX+Heat | |
| 12 | 15,16 | 1:00 PM | 1/07/10 | 7.4 | 7.64 | 255 | 38.57 | 15 | | 0.25 | 7 | 15 | 22% | Pipe SSE, MX+Heat | |
| 13 | 25,26 | 3:30 PM | 1/07/10 | 7.4 | 7.74 | 270 | 39.74 | 15 | | 0.50 | 7 | 15 | 20% | Pipe SSE, Heat | |
| 13 | 27,28 | 3:30 PM | 1/07/10 | 7.4 | 7.74 | 270 | 39.74 | 15 | | 0.50 | 7 | 15 | 25% | Pipe SSE, No MX, No Heat | In-house analyzed |
| 13 | 19,20 | 3:30 PM | 1/07/10 | 7.4 | 7.74 | 270 | 39.74 | 15 | | 1.00 | 7 | 12 | 23% | Pipe SSE, MX+Heat | *** |
| 13 | 21,22 | 3:30 PM | 1/07/10 | 7.4 | 7.74 | 270 | 39.74 | 15 | | 0.50 | 7 | 15 | 24% | Pipe SSE, MX+Heat | |

** Rate of heating was the same for different flow rates. This means that at 0.50 gal/min, biomass received less heat than that at 0.25 gal/min
*** The aim of this series of runs was to study the effect of overnight storing in darkness and cold. The same algae batch tested on 1/11/2010 was tested on 7/12

SYSTEMS AND METHODS FOR EXTRACTING NON-POLAR LIPIDS FROM AN AQUEOUS ALGAE SLURRY AND LIPIDS PRODUCED THEREFROM

FIELD OF THE INVENTION

The invention relates to the fields of energy and microbiology. In particular, the invention relates to systems, apparatus and methods for harvesting cellular mass and debris as well as intracellular products from algae cells which can be used as a substitute for fossil oil derivatives in various types of product manufacturing.

BACKGROUND OF INVENTION

The intracellular products of microorganisms show promise as a partial or full substitute for fossil oil derivatives or other chemicals used in manufacturing products such as pharmaceuticals, cosmetics, industrial products, biofuels, synthetic oils, animal feed, and fertilizers. However, for these substitutes to become viable, methods for obtaining and processing such intracellular products must be efficient and cost-effective in order to be competitive with the refining costs associated with fossil oil derivatives. Current extraction methods used for harvesting intracellular products for use as fossil oil substitutes are laborious and yield low net energy gains, rendering them unviable for today's alternative energy demands. Such methods can produce a significant carbon footprint, exacerbating global warming and other environmental issues. These methods, when further scaled up, produce an even greater efficiency loss due to valuable intracellular component degradation and require greater energy or chemical inputs then what is currently financially feasible from a microorganism harvest. For example, the cost per gallon for microorganism bio-fuel is currently approximately nine-fold over the cost of fossil fuel.

Recovery of intracellular particulate substances or products from microorganisms requires disruption or lysing of the cell transmembrane. All living cells, prokaryotic and eukaryotic, have a plasma transmembrane that encloses their internal contents and serves as a semi-porous barrier to the outside environment. The transmembrane acts as a boundary, holding the cell constituents together, and keeps foreign substances from entering. According to the accepted current theory known as the fluid mosaic model (S. J. Singer and G. Nicolson, 1972), the plasma membrane is composed of a double layer (bi-layer) of lipids, an oily or waxy substance found in all cells. Most of the lipids in the bilayer can be more precisely described as phospholipids, that is, lipids that feature a phosphate group at one end of each molecule.

Within the phospholipid bilayer of the plasma membrane, many diverse, useful proteins are embedded while other types of mineral proteins simply adhere to the surfaces of the bilayer. Some of these proteins, primarily those that are at least partially exposed on the external side of the membrane, have carbohydrates attached and therefore are referred to as glycoproteins. The positioning of the proteins along the internal plasma membrane is related in part to the organization of the filaments that comprise the cytoskeleton, which helps anchor them in place. This arrangement of proteins also involves the hydrophobic and hydrophilic regions of the cell.

Intracellular extraction methods can vary greatly depending on the type of organism involved, their desired internal component(s), and their purity levels. However, once the cell has been fractured, these useful components are released and typically suspended within a liquid medium which is used to house a living microorganism biomass, making harvesting these useful substances difficult or energy-intensive.

In most current methods of harvesting intracellular products from algae, a dewatering process has to be implemented in order to separate and harvest useful components from a liquid medium or from biomass waste (cellular mass and debris). Current processes are inefficient due to required time frames for liquid evaporation or energy inputs required for drying out a liquid medium or chemical inputs needed for a substance separation.

Accordingly, there is a need for a simple and efficient procedure for harvesting intracellular products from microorganisms that can be used as competitively-priced substitutes for fossil oils and fossil oil derivatives required for manufacturing of industrial products.

SUMMARY OF THE INVENTION

The present invention relates to methods, systems, and apparatuses for extracting non-polar lipids from microalgae and to the lipid products extracted from these methods, systems and apparatuses. The methods, systems, and apparatuses of the invention can advantageously extract the non-polar lipids from microalgae at a high volume flow rate. By extracting the non-polar lipids (e.g., triglycerides) separate from the polar lipids (e.g., phospholipids and chlorophyll) and cellular debris, the methods, systems, and apparatuses of the invention can produce a product suitable for use in traditional petrochemical processes such as petrochemical processes that utilize precious metal catalysts.

In one embodiment, the present invention relates to a method for extracting non-polar lipids from microalgae in a flowing aqueous slurry. The method includes (i) providing an aqueous slurry including microalgae; (ii) providing a lipid extraction apparatus having a body including a channel that defines a fluid flow path, at least a portion of the channel formed from a cathode and an anode spaced apart to form a gap with a distance in a range from 1 mm to 200 mm within the channel; (iii) flowing the aqueous slurry through the channel and applying an electromotive force across the gap, the electromotive force compromising the microalgae cells and releasing a lipid fraction having greater than 80 wt % non-polar lipids and less than 20 wt % polar lipids; and (iv) recovering at least a portion of the nonpolar lipid fraction.

By selecting the gap distance, voltage, amperage and flow rate, the microalgae can be lysed or otherwise compromised to release non-polar lipids without extracting the polar lipids such as the phospholipids and the chlorophyll. Moreover, since the anode and the cathode form part of the channel through which the aqueous slurry is flowing, the microalgae can be exposed to a large surface area of anode and cathode at reasonable distances, which improves the efficiency and economy of lipid extraction and allows high throughput and scalability.

In addition, since the anode and cathode form part of a channel, the duration of the algae in the field can be controlled by adjusting the flow rate in the channel (e.g., by adjusting the pumping pressure). The ability to adjusting the flow rate, amperage, and/or voltage is useful for processing microalgae because some properties of microalgae slurries can vary over time due to naturally occurring variations. Thus, the methods systems and apparatuses of the invention allow extraction that accommodates these variations.

The present invention is also directed to the lipid fraction produced from the methods, systems, and apparatuses described herein. The lipid fraction released from the microalgae cells using the methods, systems, and apparatuses of the present invention can have a unique composition due to the way in which the lipids are released. The process can be carried out by controlling the gap distance, voltage, amperage, and flow rate to release the vast majority of non-polar lipids without releasing the polar lipids. The particular voltages, amperages, and flow rates will depend on the particular aqueous slurry and species of microalgae being process. However, a visual inspection of the released lipid fraction can indicate when the polar lipids fraction is being extracted in large quantities since the undesired polar lipids (e.g., mixtures of chlorophyll and phospholipids) tend to be darker. Alternatively, the process can include sampling the released lipid fraction and analyzing the sample using high performance liquid chromatography to determine the percentage of undesired polar lipids. The flow rate, amperage, voltage, and/or gap distance can then be selected to minimize the percentage of polar lipids while maintaining suitable throughput. In one embodiment, a computer controlled lipid extraction apparatus can use HPLC data to select the parameters that minimize polar lipids in the released lipid fraction. In a preferred embodiment, the non-polar lipid content in the released fraction is greater than 90% and the polar fraction is less than 10%, more preferably the non-polar lipid content is greater than 95% and the polar lipid content is less than 5%, even more preferably the non-polar lipid content is greater than 98% and the polar lipid content is less than 2%, and most preferably the non-polar lipid content is at least 99% and the polar lipid content is less than 1%.

The composition of the released lipid fraction will also depend to some degree on to the aqueous slurry used for the feed. In one embodiment of the invention, the released lipid fraction is recovered from a process using an aqueous slurry where at least 70 wt % of the microorganisms in the slurry are microalgae (preferably at least 80 wt %, more preferably at least 90 wt %, and most preferably at least 99 wt % microalgae).

The present invention is also directed to lipid extraction apparatuses and systems. In one embodiment, the lipid extraction apparatus includes a body including a channel that defines a fluid flow path from a first opening to a second opening, the first opening providing an inlet for an aqueous algae slurry and the second opening providing an outlet for the aqueous algae slurry; a cathode, an anode, and an insulator forming at least a portion of the channel that defines the fluid flow path, the cathode and the anode being spaced apart to form a gap with a distance in a range from 1 mm to 200 mm. The anode and the cathode provide sufficient surface area at the gap distance such that the volume of the fluid flow path within the gap is at least 50 ml, preferably at least 100 ml, and most preferably at least 200 ml. The narrow gap distance and large volume of fluid flow can be achieved by either making the channel long or wide or both. However, by limiting the gap distance, the apparatus can apply an electromotive force suitable for extracting non-polar lipids, while allowing high throughput.

In one embodiment, the channel of the lipid extraction apparatus can be formed from first and second electrically conductive tubes that are configured to be a tube within a tube, where the spacing between the inner and outer tube forms the fluid flow path and the inner and outer electrically conductive tubes provide the cathode and anode of the apparatus. In this embodiment, an insulator can be placed between the first and second electrically conductive tubes to prevent a short across the tubes and to optionally direct fluid flow. In one embodiment, the apparatus includes rifling between the first and second tubes to cause a spiral flow path. This can be accomplished using a spacer, grooves, protrusions, or other suitable structure that can cause directional fluid flow between the two electrically conductive tubes.

These and other objects and features of the present invention will become more fully apparent from the following description and appended claims, or may be learned by the practice of the invention as set forth hereinafter.

BRIEF DESCRIPTION OF THE DRAWINGS

FIG. 16 is a table of data from experiments to quantify lipid extraction and identify optimal extraction parameters.

DETAILED DESCRIPTION

Figure 1:
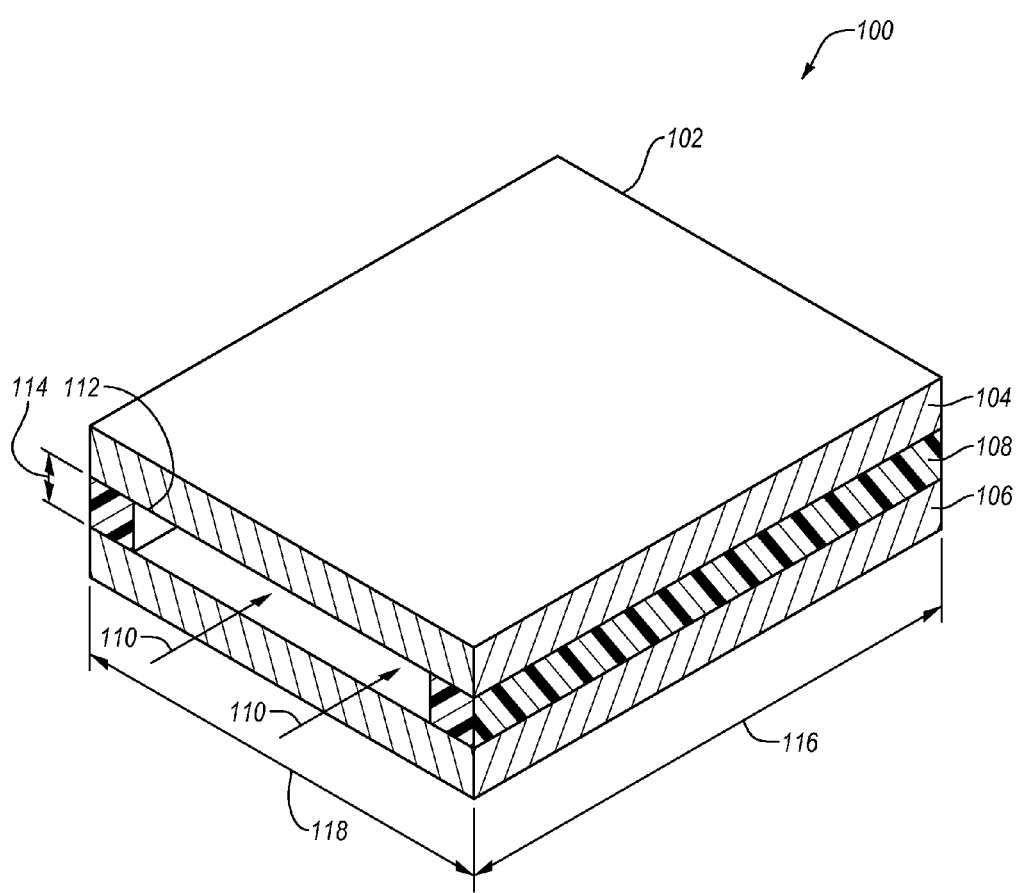
FIG. 1 illustrates a portion of a lipid extraction device according to one embodiment of the invention.

The present invention relates to methods, systems, and apparatuses for extracting non-polar lipids from microalgae and to the lipid products extracted from these methods, systems and apparatuses. The methods, systems, and apparatuses of the invention can advantageously extract the non-polar lipids from microalgae at a high volume flow rate. By extracting the non-polar lipids (e.g., triglycerides) separate from the polar lipids (e.g., phospholipids and chlorophyll) and cellular debris, the methods, systems, and apparatuses of the invention can produce a product suitable for use in traditional petrochemical processes such as petrochemical processes that utilize precious metal catalysts.

In a first embodiment, a method is described for extracting non-polar lipids from microalgae. The method generally includes (i) providing an aqueous slurry including microalgae; (ii) providing a lipid extraction apparatus having a body including a channel that defines a fluid flow path, at least a portion of the channel formed from a cathode and an anode are spaced apart to form a gap with a distance in a range from 1 mm to 200 mm within the channel; (iii) flowing the aqueous slurry through the channel and applying an electromotive force across the gap, the electromotive force compromising the microalgae cells and releasing a lipid fraction having greater than 80 wt % non-polar lipids and less than 20 wt % polar lipids; and (iv) recovering at least a portion of the non-polar lipid fraction.

In performing the method, a microalgae slurry is provided. The microalgae slurry includes water and algae. Because the process of the invention is carried out using an aqueous slurry, the costs normally associated with drying the algae before extraction can be avoided. The algae cells can be any microalgae cells, including, but not limited to, *Nanochloropsis oculata, Scenedesmus, Chlamydomonas, Chlorella, Spirogyra, Euglena, Prymnesium, Porphyridium, Synechoccus* sp, *Cyanobacteria* and certain classes of Rhodophyta single celled strains. The algae can be phototrophic algae grown in an open natural environment or in a closed environment. The methods of the invention can also be used to extract lipids from heterotrophic bacterial.

The concentration of the algae in the slurry will depend in part on the type of algae, the growth conditions, and whether the algae has been concentrated. The aqueous slurry can include be grown and used at any suitable concentration, such as, but not limited to a range from about 100 mg/L to about 5 g/l (e.g., about 500 mg/L to about 1 g/L). In some embodiments, unconcentrated algae from a growth vessel will be from 250 mg/L to 1.5 g/L and may be pre-concentrated with other conventional means to within a range from 5 g/L to 20 g/L. If desired, the microalgae concentration can be increased using any known technique. For example, concentrating can be carried out using flocculation. The flocculation can be a chemical flocculation or electro-flocculation or any other process that effectuates a similar function.

In one embodiment, the algae slurry has a desired concentration of microalgae as a percentage of the total microorganisms in the slurry. The purity of the slurry with respect to the concentration of microalgae can impact the composition of the lipids released from the extraction process. In a preferred embodiment, at least 70 wt % of microorganism within the aqueous slurry are microalgae, preferably at least 80 wt %, more preferably at least 90 wt %, even more preferably at least 95 wt %, and most preferably at least 99 wt %.

The pH of the slurry during extraction can vary. However, in one embodiment, the pH is alkaline. Acid or base can be added to keep the pH can be kept in a range from 6.6-9.0, 6.8-8.6, or 7.0-8.5.

In a second step, a lipid extraction apparatus is provided that includes an anode and a cathode that form a channel through which the aqueous slurry can flow. FIG. 1 is a schematic of a portion of a lipid extraction device 100 that is suitable for use in the method of the invention. The portion of extraction device 100 includes a body 102 that has an anode 104 and a cathode 106 electrically separated by an insulator 108. Anode 104 and cathode 106 are spaced apart to form a channel 112 that defines a fluid flow path 110. Channel 112 has a length 116 that extends the length of the anode and cathode exposed to the fluid flow path 110. Channel 112 also has a width 118 that is defined by the space between the insulators that is exposed to the anode 104 and cathode 106. The gap 114 between anode 104 and cathode 106 has a distance suitable for applying an emf through the aqueous algae slurry. In one embodiment, gap 114 is in a range from 0.5 mm to 200 mm, preferably 1 mm to 50 mm, more preferably 2 mm 20 mm. The narrow gap distance coupled with a large width 118 and length 116 can provide a large volume for channel 112 while maintaining a strong electrical field for compromising the algae cells to release polar lipids. The length 116 of channel 112 is the dimension in the direction of fluid flow 110 and can be any length so long as channel is not hampered by plugging or significant pressure drops. In one embodiment, the length 116 of channel 112 is at least 25 cm, preferably 50 cm, more preferably 100 cm, and most preferably at least 200 cm. In one embodiment the length 116 can be less than 1000 cm, less than 500 cm or less than 250 cm. The width can be any width so long as the materials of the anode and cathode are sufficiently strong to span the width without contacting one another. In a preferred embodiment, the volume of the channel between the anode and cathode and within the gap distance 114, (i.e., the gap volume) is at least 50 ml, more preferably at least 200 ml, even more preferably at least 500 ml, and most preferably at least 1 liter. In one embodiment, the surface area of the anode and the cathode exposed to the fluid flow is at least 500 $cm^2$, preferably at least 1000 $cm^2$, and more preferably at least 2000 $cm^2$.

The anode 104 and cathode 106 can be made of any electrically conductive material suitable for applying emf across the gap, including but not limited to metals such as steel and conductive composites or polymers.

The shape of the anode and cathode can be planer or cylindrical or other shape. As described more fully below, an annulus created between an inner metallic surface of a tube and an outer surface of a smaller metallic conductor tube placed within the large tube is preferred for its ability to avoid fouling and to maintain a high surface area in a compact design. The tubes need not have a circular periphery as an inner or outer tube may be square, rectangular, or other shape and the tube shape does not necessarily have to be the same, thereby permitting tube shapes of the inner and outer tubes to be different. In a most preferred embodiment, the inner conductor and outer tube are concentric tubes, with at least one tube, preferably the outer tube, being provided with a plurality of spiral grooves separated by lands to impart a rifling to the tube. This rifling has been found to decrease build-up of residue on the tube surfaces. In commercial production, there may be a plurality of inner tubes surrounded by an outer tube to increase the surface contact of the metal conductors with the algae.

Furthermore, the use of electrical insulators, such as plastic tubes, baffles, and other devices, can be used to separate a large lipid extraction devices into a plurality of zones, so as to efficiently scale-up the invention to commercial applications.

In performing the method, the aqueous algae slurry is fed through the channel along the fluid flow path between the anode and cathode (i.e., through the gap). Power is applied to the anode and cathode to produce an electromotive force that compromises or lyses the algae cells to release the non-polar lipids (also referred to herein as "single step extraction" or "SSE"). For a given gap distance or channel volume between the anode and cathode, the amperage, flow rate, and voltage are selected to effectuate the release of the non-polar lipids.

Figure 2:
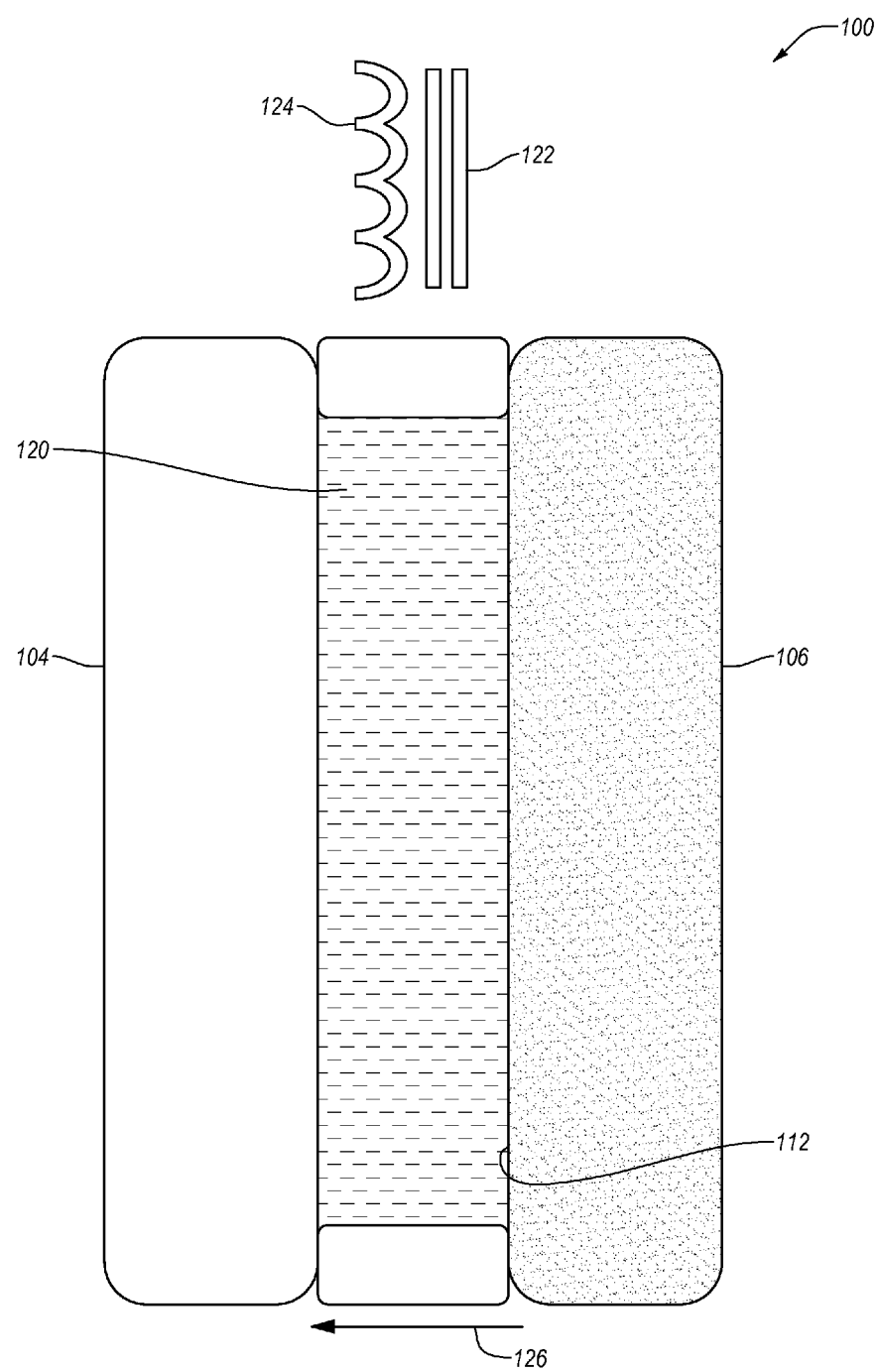
FIG. 2 illustrates a sectional perspective view of biomass flowing in between the to anode and cathode wall surfaces of the device of FIG. 1.
Figure 3:
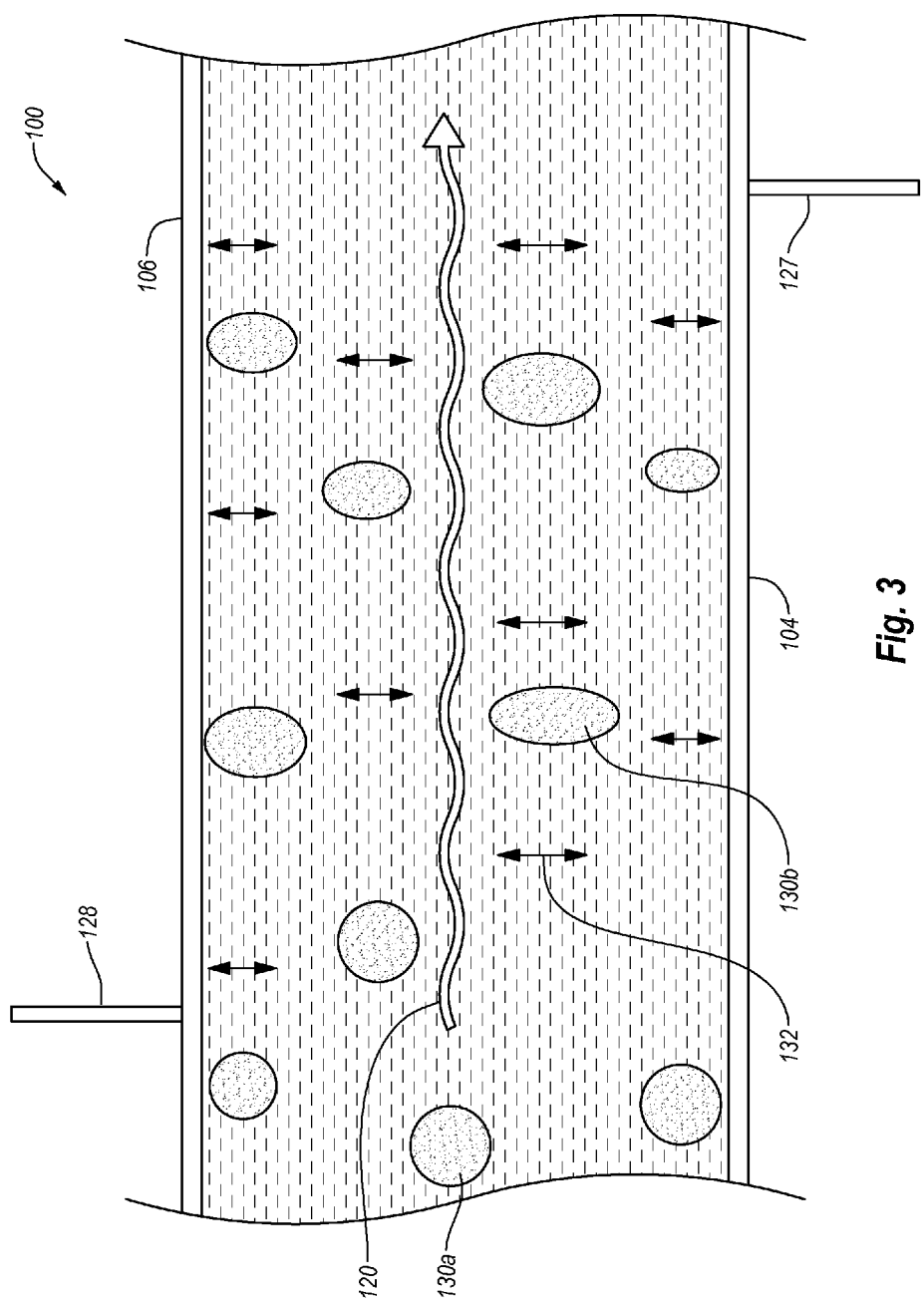
FIG. 3 illustrates a lipid extraction apparatus with a flowing liquid medium containing a microorganism biomass being exposed to an electromagnetic field caused by an electrical transfer.

Referring to FIG. 2, apparatus 100 is shown in cross section with an aqueous algae slurry 120 disposed between cathode 106 and anode 104. The aqueous algae slurry 120 is caused to flow through channel 112 using a pump (not shown). By way of an electrical conduit, a negative connection 122 is made to the anode 104, which provides electrical grounding. Positive electrical input 124 also delivered by way of a conduit connection provide positive electrical transfer throughout the cathode 106. When a positive current 124 is applied to the cathode 106 it then seeks a grounding circuit for electrical transfer as indicated by arrow 126 or in this case, to the anode 104, which allows the completion of the electrical circuit. In this respect, transfer of electrons occurs between the positive and negative surfaces areas but only when an electrically conductive liquid is present between them. As the liquid medium containing the algae slurry 120 is flowed between the surface areas, electrical transfer from the cathode 106 through the slurry 120 to the anode 104 is made. As a liquid containing a microorganism biomass transverses the anode and cathode circuit, the cells are exposed to the electric field that causes expansion and contraction of the cells In reference to FIG. 3, a simplified schematic is used to illustrate an emf transfer between two electrical conductive metal pieces with a liquid medium containing a living microorganism biomass flowing between them in a method for harvesting biomass from an aqueous solution containing algae cells. The cathode 106 requires a positive electrical connection point 128, which is used for positive current input. Positive transfer polarizes the entire length and width of the cathode 106 and seeks a grounding source in anode 104. In order to complete an electrical circuit, the anode 104 includes a grounding connection point 127, which allows an electrical transfer 132 to occur through aqueous slurry 120. The aqueous slurry includes a liquid medium that contains a nutrient source mainly composed of a conductive mineral content that was used during a growth phase of the algae in aqueous slurry 120. The liquid medium containing the nutrient source further allows positive electrical input to transfer between the cathodes 106 through the liquid medium/biomass 120 to the anode 104 and which only occurs when the liquid medium is present or flowing. Electrical input causes cellular elongation such as the distention shown in algae 130b as compared to algae 130a.

Figure 4:
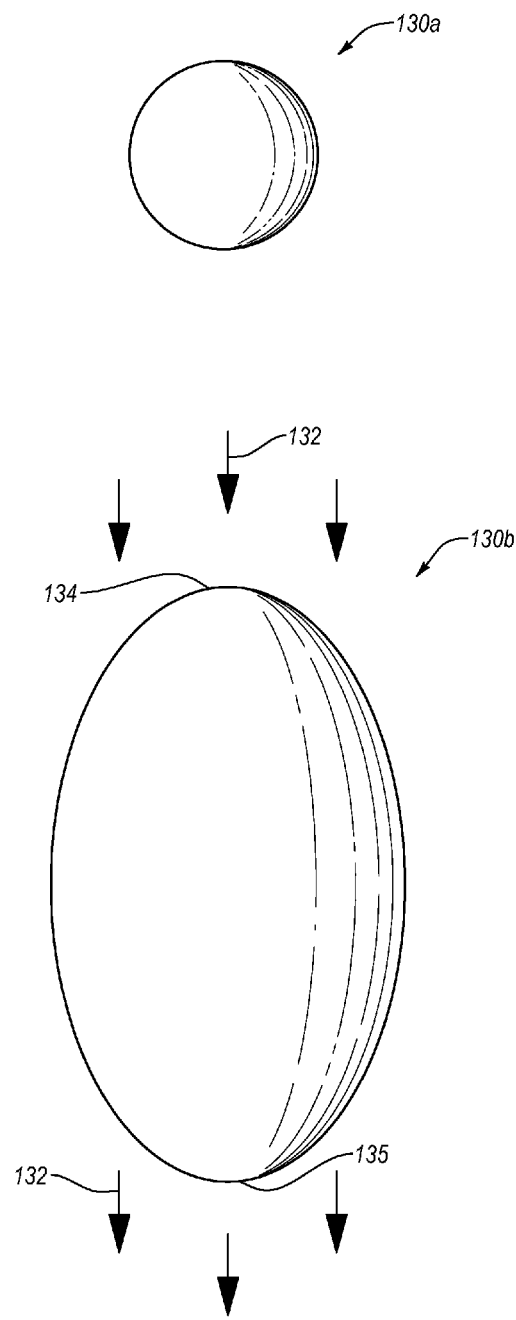
FIG. 4 illustrates an overview of a normal sized microorganism cell in relationship to a secondary illustration of a swollen cell during exposure to an electromagnetic field and electrical charge.

In reference to FIG. 4, a simplified illustration is used to exhibit the difference between a normal sized microalgae cell 130a in comparison to a microalgae cell 130b, which has been extended by the electrical field between the cathode and anode. During the electrical "on" phase, emf 132 (FIG. 3) polarizes the algae cell walls and/or membranes. A positive charge and a negative charge develop on the membrane of respective ends 134 and 135 of algae cell 130b in alignment with the emf field 132. The dipole on the cells causes the cells to be pulled apart along the electrical field lines until the cell wall/membrane is compromised, thereby releasing the cell contents. This elongation eventually causes external structural damage to the exterior wall with general damage resulting in a wall and membrane that is permeable to the intracellular fluids and/or causes lysis. The flow rate, voltage, and amperage, are selected in combination with the gap distance and composition of the aqueous slurry to cause release of primarily the polar lipids without releasing the non-polar lipids such as those in the cell membrane and the chlorophyll. A visual inspection or high performance liquid chromatography can be used to monitor the lipid content to minimize the polar lipid fraction as compared to the non-polar lipid fraction.

In one the flow rate through the gap volume (i.e., the portion of the channel in the electric field at the gap distance) is 0.1 ml/second per ml of gap volume, more preferably at least 0.5 ml/second per ml of gap volume, even more preferably at least 1.0 ml/second per ml of gap volume and most preferably at least 1.5 ml/second per ml of gap volume. In one embodiment the flow rate can be controlled controlling the pressure using a pump or other suitable fluid flow mechanical devices.

The average amperage can be at least 1 amp, 5 amps, 10 amps, 50 amps, or even at least 100 amps. The maximum amps can be less than 200 amps, less than 100 amps, less than 50 amps, or less than 10 amps. The range of amperage can be any range from the foregoing maximum and minimum amperages.

The voltage can be at least 1V, 10V, 100V, 1 kV, or even at least 20 kV. The maximum voltage can be less than 50 kV, less than 30 kV, less than 10 kV, less than 1 kV, or less than 100V. The range of voltage can be any range of the foregoing maximum and minimum voltages.

An example of a suitable configuration for extracting non-polar lipids includes an apparatus with a gap distance of $\frac{1}{16}$-$\frac{1}{4}$ inch and a gap volume of 250 ml-1000 ml and an electrical current of 1-60 peak amps @ 1-24 volts or 25 w to 500 watts. The flow volume can be at a rate of 1 gallons per minute (GPM) of throughput with a culture having a density of 500 mg/L, one would use approximately 70 watts of energy (3.5 v @ 20 peak amps) for a successful extraction. At 5 GPM, the same culture could be extracted using approximately 350 watts (3.5 v @ 100 peak amps).

In another example, at 0.5 GPM, 500 mg/L density, an electrical current of approximately 60 watts (15 peak amps @ 4 volts) is applied. Generally, a GPM of approximately 0.1 to approximately 5 GPM and watts in the range of about 20 to about 1000 watts (e.g., 2-18 volts @ 2-50 peak amps) are used. For example, at 1 GPM of throughput with a culture having a density of 500 mg/L, one could use approximately 70 watts of energy (3.5 v @ 20 peak amps) for a successful extraction. At 5 GPM, the same culture would require approximately 350 watts (3.5 v @ 100 peak amps).

In one embodiment, the emf can be pulsed on and off repeatedly to cause extension and relaxation of the algae cells. In this embodiment, voltages can be higher and peak amperage lower while average amperage remains relatively low. This reduces the energy requirements for operating the apparatus and reduces wear on the anode and cathode. In one embodiment, the frequency of the emf pulses is at least about 500 Hz, 1 kHz, 2 kHz, or 30 kHz. The frequency can be less than 200 kHz, 80, kHz, 50 kHz, 30 kHz, 5 kHz, or 2 kHz. Ranges for the pulse frequency can be any combination of the foregoing maximum and minimum frequencies.

The temperature of the aqueous slurry during extraction can also have an impact on the power required to extract the non-polar lipids. Lipid extraction may be carried out at room temperature. However, in one embodiment, heat is added to the aqueous algae slurry to achieve a desired temperature. Lipid extraction may be carried out at a temperature above 40° F., 65° F., 80° F., 100° F., or 120° F. The temperature can be below 130° F., 115° F., 105° F., or 90° F. Ranges for the extraction temperature can be any combination of the foregoing maximum and minimum temperatures.

The temperature of the slurry can also be adjusted to control the specific gravity of the water relative to the algae (the specific gravity of water density is optimal at 40 degrees F.).

As the liquid medium (typically mainly composed of water) is heated, alterations to its hydrogen density occurs; this alteration of density allows a normally less dense material to sink or in this case, heavier fractured cellular mass and debris materials which would normally float, now rapidly sink to the bottom of the liquid column This alteration also allows easier harvesting of these materials which are also useful for other product applications. Once the EMP and heating process has been achieved, the liquid medium containing a now fractured biomass is transferred into a secondary holding tank where a liquid pump allows a continuous loop flow. As used in this description "specific gravity" is a dimensionless unit defined as the ratio of density to a specific material as opposed to the density of the water at a specified temperature.

Figure 5:
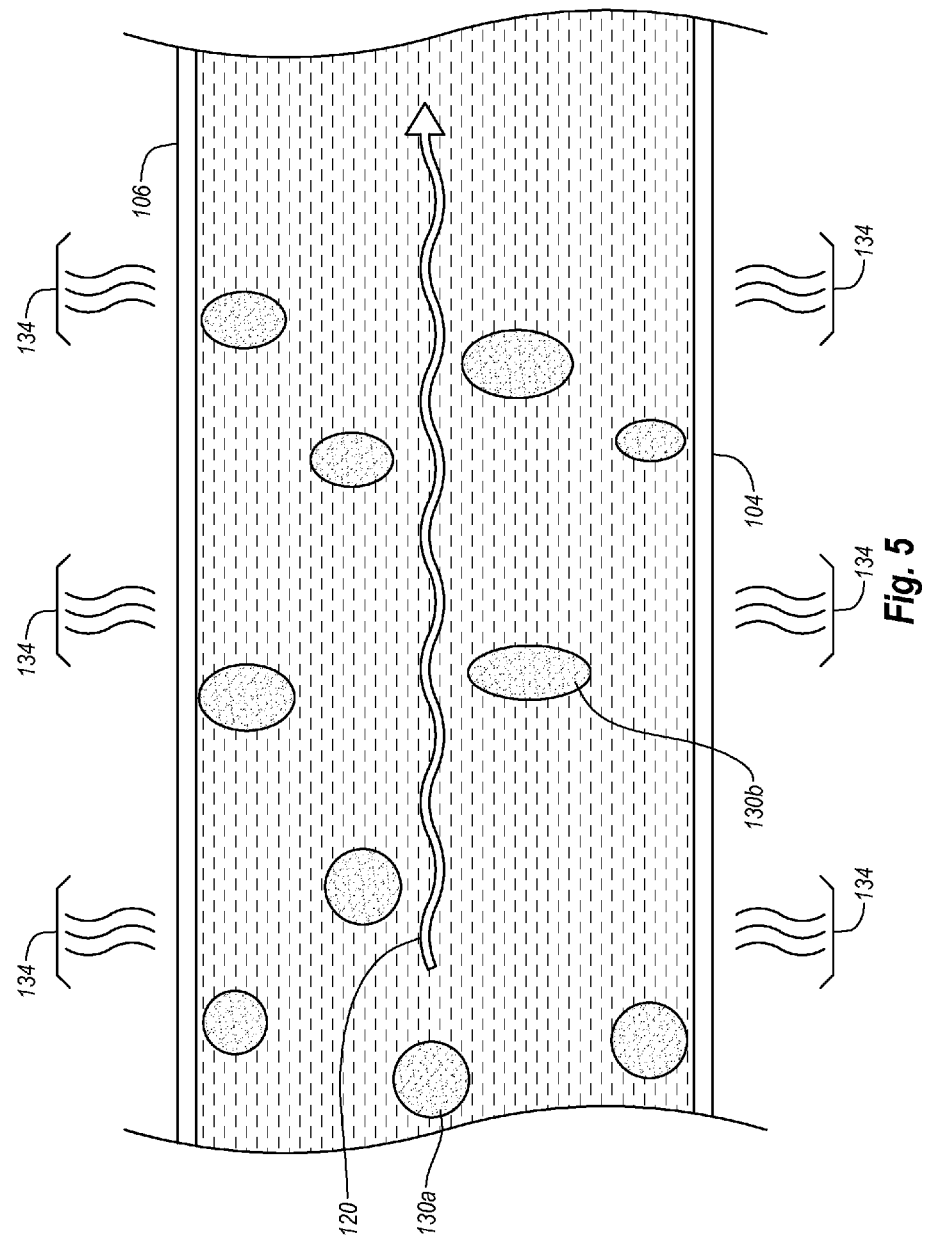
FIG. 5 illustrates the lipid extraction apparatus of FIG. 4 with heat being applied and transferred into the liquid medium.

In reference to FIG. 5, a simplified schematic is used to illustrate a heat transfer example between the outer walls of the cathode 106 and/or anode 104 and into the liquid medium/biomass during the EMP process in a method for harvesting cellular mass and debris from an aqueous solution containing algae cell. An applied heating device 134 attaches to the outside wall surfaces of the cathode 106 and anode 104, which allows heat transfer to penetrate into the aqueous slurry 120.

The products recovered from the methods of the present invention can have a relatively low content of polar lipids such as chlorophyll and phospholipids. In a preferred embodiment the lipid extraction according to the present invention is carried out to produce a released lipid fraction with a non-polar lipid content greater than 90% and the polar fraction is less than 20%, preferably the non-polar lipid content in the released fraction is greater than 90% and the polar content is less than 10%, even more preferably the non-polar lipid content is greater than 95% and the polar lipid content is less than 5%, yet even more preferably the non-polar lipid content is greater than 98% and the polar lipid content is less than 2%, and most preferably the non-polar lipid content is at least 99% and the polar lipid content is less than 1%.

The methods of the invention may further include reducing the content of phosphorus to less than 100 ppm, preferably less than 20 ppm and most preferably less than 10 ppm and using the non-polar lipids in at least one catalytic refining process. For example, the lipids can be hydrotreated using a supported catalyst.

In one embodiment, the method of extracting lipids can be carried out by periodically drawing algae from a growing algae source to maintain a steady rate of growth. Steady state growth can be achieved by drawing algae at a rate of less than half the algae mass per unit time that it takes for the algae to double. In one embodiment algae is harvest at least as often as the doubling time of the algae, more preferably at least twice during the doubling time of the algae. The doubling time will depend on the algae type and growth conditions but can be as little as 6 hours to several days.

Figure 6:
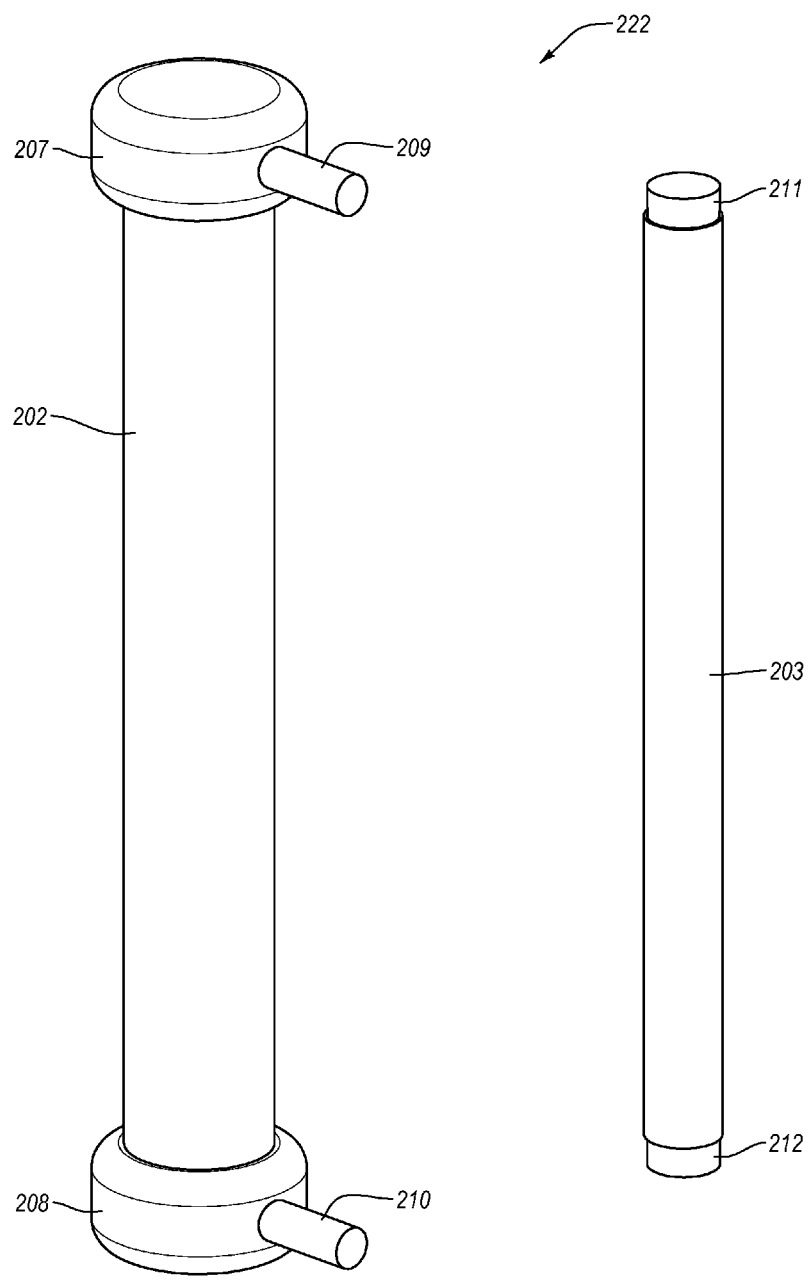
FIG. 6 illustrates a perspective view of the anode and cathode tubes of an apparatus according to one embodiment of the invention.
Figure 7:
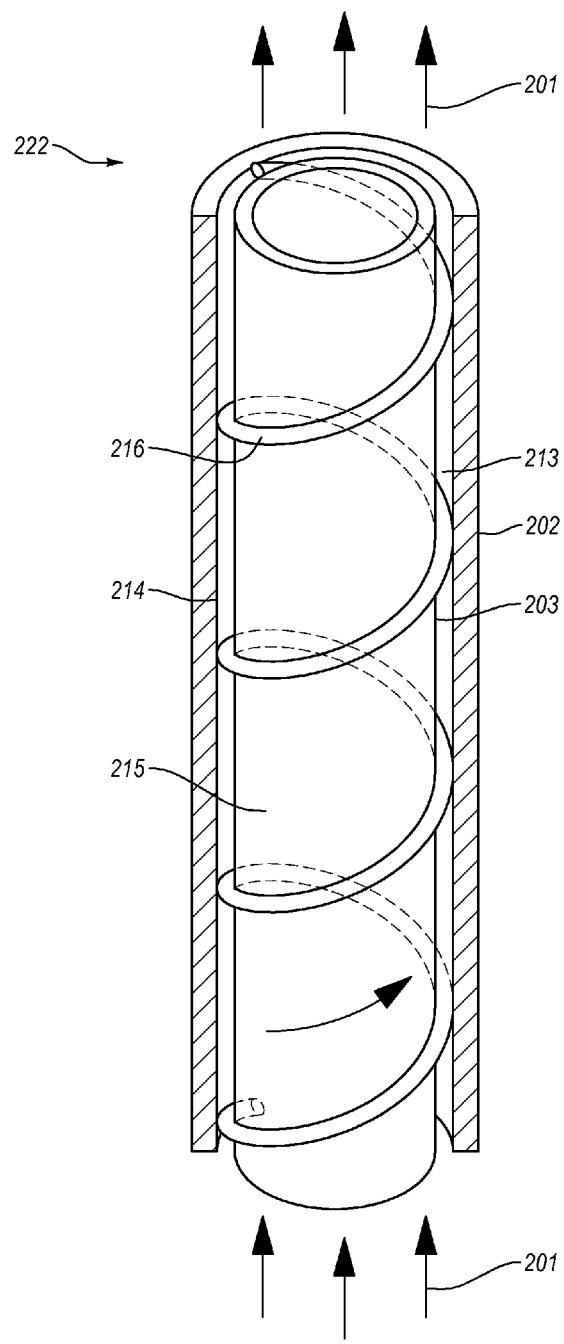
FIG. 7 illustrates a perspective sectional view of the apparatus of FIG. 6 and including a spiral spacer in between the anode and cathode tubes.
Figure 8:
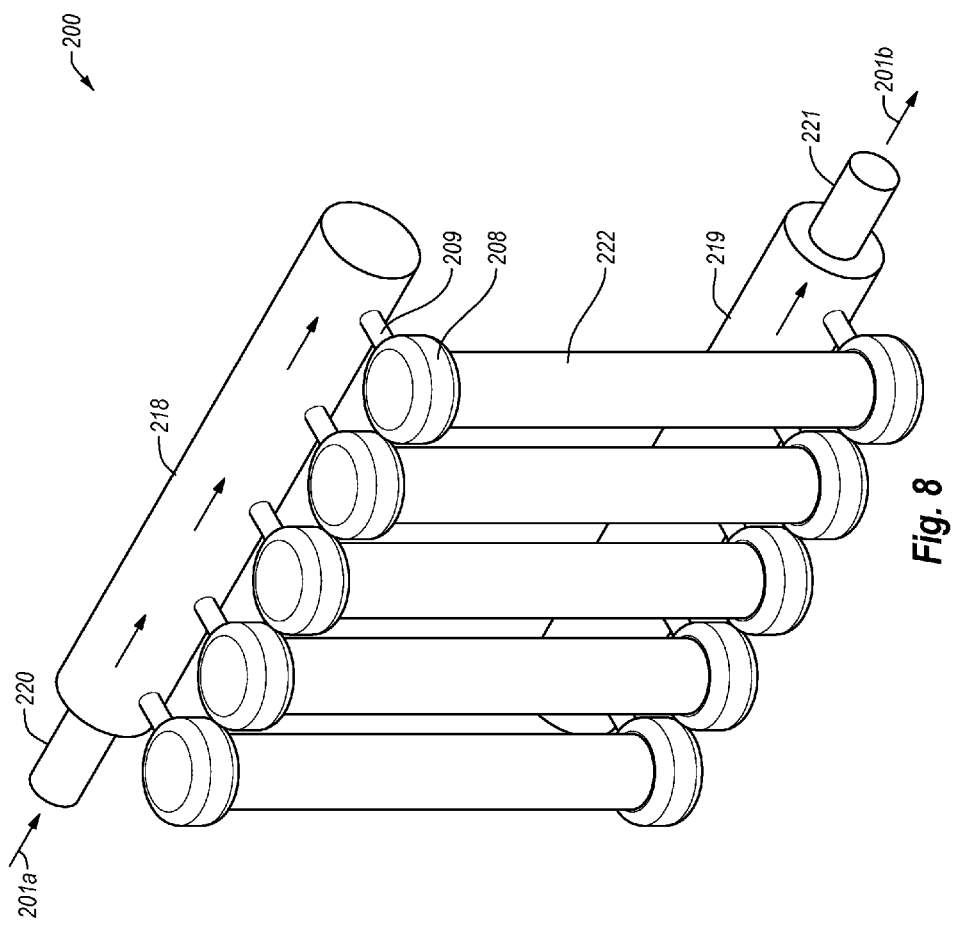
FIG. 8 is a perspective view of a series of lipid extraction devices of FIG. 7 connected in parallel by an upper and lower manifold.

FIGS. 6-8 describe an example lipid extraction apparatus in more detail. The apparatus 222 shown in FIGS. 6-8 illustrate a "tube within a tube" configuration. FIG. 6 illustrates a disassembled lipid extraction device showing a first conductive tube 203 (hereinafter cathode 203, although conductive tube 203 may also be the anode or switch between anode and cathode) that is configured to be placed in a second conductive tube 202 (hereinafter anode 202, although conductive tube 202 may also be the cathode or switch between anode and cathode). The outer anode tube 202 includes a pair of containment to sealing end caps 207 and 208. Sealing end cap 207 provides an entry point 209 used to accept an aqueous algae slurry. After biomass transiting, the opposing end cap 208 provides an exit point 210 to the outward flowing algae biomass.

As shown also in FIG. 6, the inner cathode tube 203 includes sealed end caps 211 and 212 to prevent liquid flow through the center of the tube and to divert the flow between the inner surface of anode 202 and the outer surface of cathode 203, thereby forming a channel. The channel can be sized and configured as described above with respect to FIG. 1. The use of a "tube within a tube" configuration is particularly advantageous for avoiding fouling by the algae and/or other organism in the slurry.

FIG. 7 shows an alternative embodiment in which an insulative spacer 213 that is positioned in the channel between the anode and cathode to cause spiraling fluid flow. Insulative spiraling isolator spacer 213 serves as a liquid seal between the two wall surfaces 214 and 215 with the thickness of the spacer preferably providing equal distance spacing between the anode 202 and the cathode 203. The spacing and directional flow can cause the fluid flow path to complete three hundred and sixty degree transfer of electrical current around the anode 202 and cathode tube 203. The spacer 213 can also help prevent contact between the anode 202 and cathode 203, which prevents shorting the anode and the cathode and forces electrical current through the liquid medium. Further the spiraling isolator 213 now provides a gap 216 between the two wall surfaces 214 and 215 allowing a passage way for a flowing biomass 201. The spiraling directional flow further provides a longer transit duration which provides greater electrical exposure to the flowing biomass 1 thus increasing substance extraction efficiency at a lower per kilowatt hour consumption rate during intracellular substance extraction. Any suitable material can be used as a spacer. Typically, ceramic, polymeric, vinyl, PVC plastics, bio-plastics, vinyl, monofilament, vinyl rubber, synthetic rubber, or other non-conductive materials are used.

In reference to FIG. 8, a series of anode and cathode circuits 222 are shown in parallel having a common upper manifold chamber 218 which receives an in flowing biomass 1 through entry port 20. Once entering into the upper manifold chamber 218, the biomass 1 makes a downward connection into each individual anode and cathode circuit 222 through entry ports 209 which allow a flowing connection to the sealing end caps 208. It is at this point where the flowing biomass 201 (i.e., aqueous algae slurry) enters into the anode and cathode circuits 222. Once transiting in spiral through the individual circuits 222, the flowing biomass 201 exits into a lower manifold chamber 219 where the biomass 201 is then directed to flow out of the apparatus 200 (system) through exit point 221.

Figure 9:
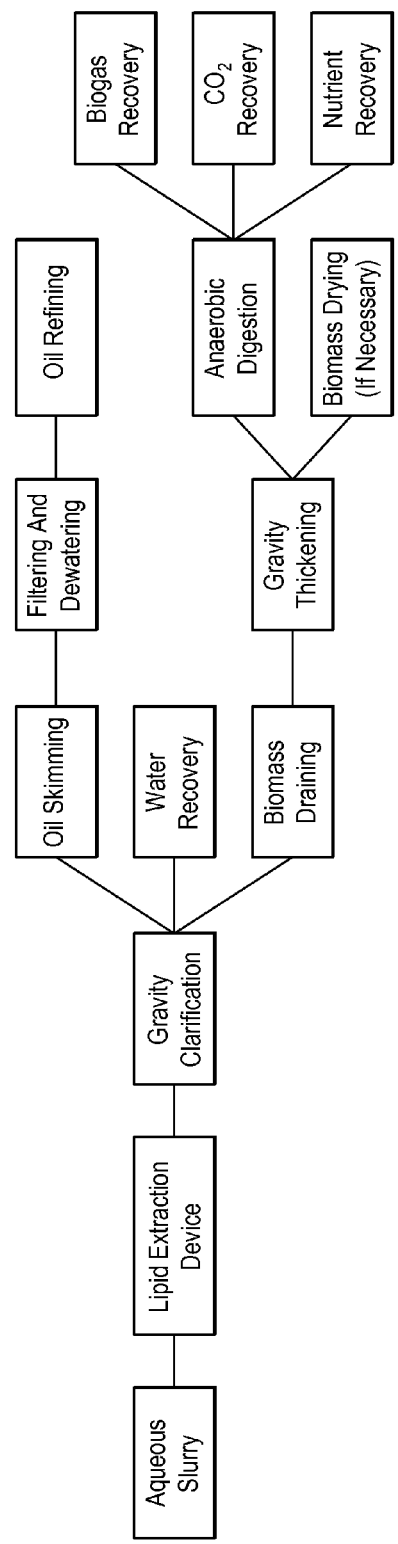
FIG. 9 depicts a general flow diagram illustrating various steps of a process for extracting non-polar lipids from microalgae according to one embodiment of the present invention.

With Reference to FIG. 9, an overall process is described for extracting and processing lipids. The methods, systems, and apparatuses of the invention can use all or a portion of the steps and apparatuses shown in FIG. 1. In a method of harvesting at least one intracellular product from algae cells in aqueous suspension, the cells are grown in a growth chamber. A growth chamber (also referred to herein as a "reactor") can be any body of water or container or vessel in which all requirements for sustaining life of the algae cells are provided for. Examples of growth chambers include an open pond or an enclosed growth tank. The growth chamber is operably connected to an apparatus 200 as described herein such that algae cells within the growth chamber can be transferred to the apparatus 200, e.g., by way of gravity or a liquid pump, the living bio mass is flowed via a conduit into the inlet section of the anode and cathode circuit. Algae cells within the growth chamber can be transferred to the apparatus 200 by any suitable device or apparatus, e.g., pipes, canals, or other conventional water moving apparatus. In order to harvest at least one intracellular product from the algae cells, the algae cells are moved from the growth chamber to an apparatus 200 (or other apparatus as described above with reference to FIGS. 1-8) and contained within the apparatus 200. When added to the apparatus 200, the algae cells are generally in the form of a live slurry (also referred to herein as "biomass"). The live slurry is an aqueous suspension that includes algae cells, water and nutrients such as an algal culture formula based on Guillard's 1975 F/2 algae food formula that provides nitrogen, vitamins and essential trace minerals for improved growth rates in freshwater and marine algae. Any suitable concentration of algae cells and sodium chloride, fresh, brackish or waste water can be used, such that the algae cells grow in the aqueous suspension.

After the non-polar lipid fraction is released in apparatus 200, the released lipid fraction may be subjected to one or more downstream treatments including gravity clarification. Gravity clarification generally occurs in a clarification tank in which the intracellular product(s) of interest (e.g., lipids) rises to the top of the tank, and the cellular mass and debris sinks to the bottom of the tank. In such an embodiment, upon transiting the circuit, the fractured cellular mass and debris is flowed over into a gravity clarification tank that is operably connected to an apparatus 200 for harvesting cellular mass and debris and intracellular products from algae cells as described herein. In the gravity clarification tank, the lighter, less dense substances float to the top of the liquid column while the heavier, denser remains sink to the bottom for additional substance harvest.

The intracellular product(s) of interest is then easily harvested from the top of the tank such as by skimming or passing over a weir, and the cellular mass and debris can be discarded, recovered and/or further processed. A skimming device then can be used to harvest the lighter substances floating on the surface of the liquid column while the heavier cellular mass and debris remains can be harvested from the bottom of the clarification tank. The remaining liquid (e.g., water) can be filtered and returned to the growth chamber (recycled) or removed from the system (discarded).

In an embodiment in which the intracellular product is oil (i.e., lipids), the oil can be processed into a wide range of products including vegetable oil, refined fuels (e.g., gasoline, diesel, jet fuel, heating oil), specialty chemicals, nutraceuticals, and pharmaceuticals, or biodiesel by the addition of alcohol. Intracellular products of interest can be harvested at any appropriate time, including, for example, daily (batch harvesting). In another example, intracellular products are harvested continuously (e.g., a slow, constant harvest). The cellular mass and debris can also be processed into a wide range of products, including biogas (e.g., methane, synthetic gas), liquid fuels (jet fuel, diesel), alcohols (e.g., ethanol, methanol), food, animal feed, and fertilizer.

In addition to gravity clarification, any suitable downstream treatment can be used. Possible downstream treatments are numerous and may be employed depending on the desired output/use of the intracellular contents and/or bio cellular mass and debris mass. For example, lipids can be filtered by mechanical filters, centrifuge, or other separation device, for example, then heated to evacuate more water. The lipids can then be further subjected to a hexane distillation. In another example, cellular mass and debris can be subjected to an anaerobic digester, a steam dryer, or belt press for additional drying for food, fertilizer etc. As shown in FIG. 9, downstream treatments also include, e.g., polishing and gravity thickening.

Figure 10:
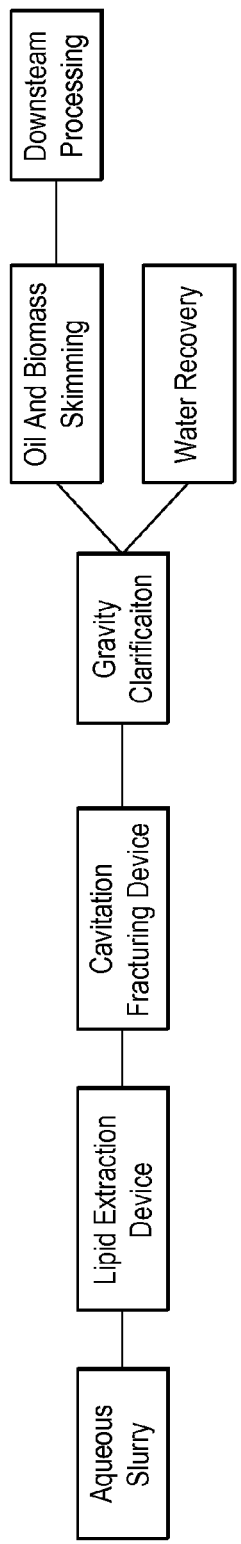
FIG. 10 depicts a general flow diagram illustrating various steps of a process for extracting non-polar lipids from microalgae according to one embodiment of the present invention.

In one embodiment, the present invention includes a method of harvesting cellular mass and debris from an aqueous solution containing algae cells by subjecting algae cells to pulsed emf and to cavitation (i.e., microbubbles) in an apparatus as described herein, resulting in a mixture that includes both intracellular product(s) (e.g., lipids) and cellular mass and debris. A process flow diagram that includes a cavitation step is shown in FIG. 10. The methods and apparatus of this embodiment can use any of the lipid extraction devices described herein. The cells can be subjected to cavitation before application of (upstream of) pulsed emf (i.e., "EMP"), or they may be subjected to cavitation concomitantly with EMP (see FIG. 15 that depicts the cavitation device electrified as it would be the EMP conductor). In one embodiment, a cavitation device includes an anode, cathode and venture mixer (all in one). In this embodiment, the cavitation unit is reduced (e.g., by half), a non-conductive gasket is added, and it is electrified. Under normal pressure conditions, e.g., under 100 psi, no effect was observed when cavitation was applied upstream of EMP, however, at pressures above 100 psi (e.g., 110, 115, 120, 130, 140, 150, 200, 300, 400 psi, etc.), it may have an effect.

In the method where cavitation is used, a micron mixing device, such as a static mixer or other suitable device such as a high throughput stirrer, blade mixer or other mixing device is used to produce a foam layer composed of microbubbles within a liquid medium containing a previously lysed microorganism biomass. Any device suitable for generating microbubbles, however, can be used. Following micronization, the homogenized mixture begins to rise and float upwards. As this mixture passes upwards through the liquid column, the less dense valuable intracellular substances freely attach to the rising bubbles, or due to bubble collision, into a heavier sinking cellular mass and debris waste, (now allowed to sink due to heated water specifics). The rising bubbles also shake loose trapped valued substances (e.g., lipids) which also freely adhere to the rising bubble column. Once the foam layer containing these useful substances has risen to the top of the liquid column, they now can be easily skimmed from the surface of the liquid medium and deposited into a harvest tank for later product refinement. Once the foam layer rises to the top of the secondary tank, the water content trapped within the foam layer generally results in less than 10% (e.g., 5, 6, 7, 8, 9, 10, 10.5, 11%) of the original liquid mass. Trapped within the foam are the less dense useful substances, and the foam is easily floated or skimmed off the surface of the liquid medium. This process requires only dewatering of the foam, rather than evaporating the total liquid volume needed for conventional harvest purposes. This drastically reduces the dewatering process, energy or any chemical inputs while increasing harvest yield and efficiency as well as purity. In this method, water can be recycled to the growth chamber or removed from the system. Cellular mass and debris can be harvested at any appropriate time, including, for example, daily (batch harvesting). In another example, cellular mass and debris is harvested continuously (e.g., a slow, constant harvest).

Once the liquid medium has achieved passage through the EMP apparatus, it is allowed to flow over into a secondary tank (or directly into a device that is located near the bottom of the tank). In this method of dewatering, the secondary tank is a tank containing a micron bubble device or having a micron bubble device attached for desired intracellular component separation and dewatering. After transmembrane lysis, a static mixer or other suitable device (e.g., any static mixer or device which accomplishes a similar effect producing micro-bubbles) is used and is located at the lowest point within a secondary tank. When activated, the static mixer produces a series of micron bubbles resulting in a foam layer to develop within the liquid medium. As the liquid medium is continuously pumped through the micro mixer, bubbled foam layers radiate outwards through the liquid and begin to rise and float upwards. The less dense desired intracellular components suspended within the liquid medium attach to the micron bubbles floating upwards and flocculate to the surface or are detached from heavier sinking biomass waste, (allowed to sink due to specific gravity alterations) due to rising bubble collision within the water column.

Figure 11:
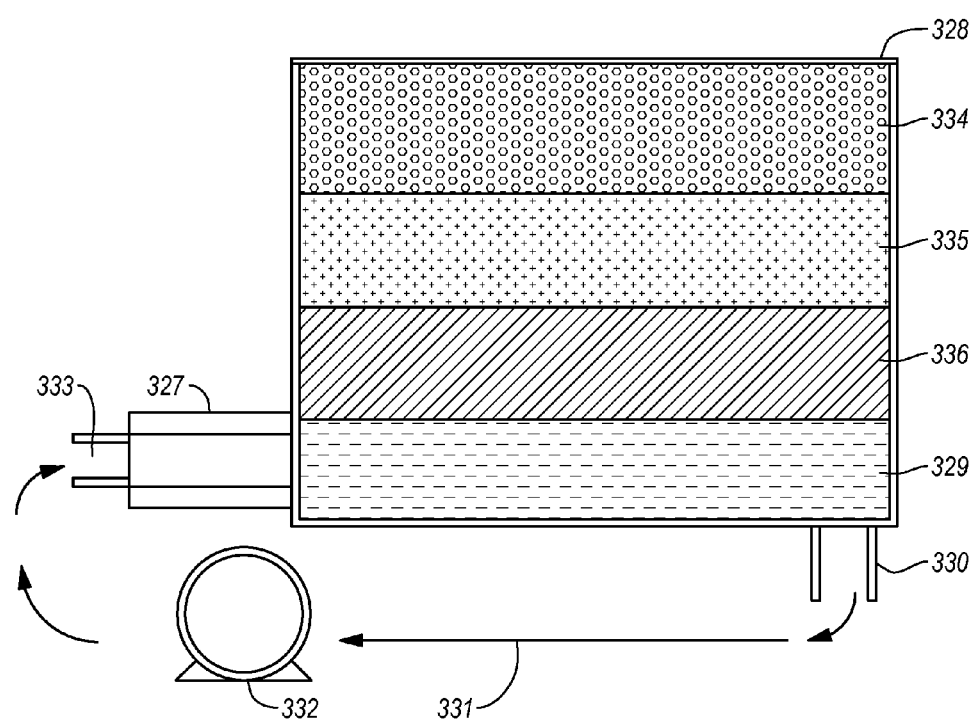
FIG. 11 Illustrates a side view of a micron mixer in association with a secondary tank containing a biomass and sequences of developing foam layers generated by a micron mixer.

In this embodiment, FIG. 11 illustrates a lower mounting location for a micron mixer 327 when in association with secondary tank 328 and containing a previously fractured biomass 329 suspended within a liquid medium. This liquid medium is then allowed to flow through a lower secondary tank outlet 330 where it is directed to flow through conduit 331 having a directional flow relationship with a liquid pump 332. Due to pumping action, the liquid is allowed a single pass through, or to re-circulate through the micron mixer via a micron mixer inlet opening 333. As liquid continues to flow through the micron mixer 327, microscopic bubbles 334 are produced which radiate outwards within the liquid column 335, forming a foam layer 336. As the process continues, the composed layer starts to rise upwards towards the surface of the liquid column 335. Once the foam layer 336 starts its upward journey towards the surface of the liquid column 335, the pump 332 is shut down, and thus the micronization process is complete. This allows all micron bubbles 334 produced at the lower exit point of the micron mixer 327 to rise to the surface and as they do, they start collecting valuable intracellular substances released into the liquid medium during the EMP process. This upward motion of the micron bubbles 334 also rubs or bumps into heavier downward-sinking cellular mass and debris, further allowing the release of trapped lighter valuable substances that have bonded with heavier-sinking cellular mass and debris remains. Once detached, these substances adhere to the micron bubbles 334 floating upwards towards the surface.

In reference to FIG. 10, a simple illustration is used to show a method for harvesting a foam layer 436 containing approximately ten percent of the original liquid medium mass/biomass 401. As the foam layer 436 containing the valuable intracellular internal substances rises to the surface of the liquid medium 435, a skimming device 437 can be used to remove the foam layer 436 from the surface 438 of liquid medium 435. The skimming device 437 located at the surface area of the secondary tank 428 allows the foam layer 436 to be pushed over the side wall of the secondary tank 428 and into a harvesting to container 439 where the foam layer 436 is allowed to accumulate for further substance harvesting procedures.

FIG. 11 illustrates one embodiment of a method and apparatus (system) as described herein for the harvest of useful substances from an algae biomass. Microorganism algae are grown in a containment system 540 and at the end of an appropriate growth cycle are transferred into the substance recovery process. The algae biomass are flowed through an optional micron bubble cavitation step 541, used to soften the outer cellular wall structure prior to other bio substance recovery processes.

After the cavitation step 541 an optional heat process 542 can be applied to change the gravity specifics of the liquid feed stock water containing the biomass. The heat option 542 allows a faster transfer of particular substances released during the harvest process. After the biomass has reached an appropriate heat range, it is then allowed to flow through an electromagnetic pulse field, the EMP station 543 where transiting biomass cells are exposed to the electromagnetic transfers resulting in the fracturing of the outer cellular wall structures.

Once flowed through the EMP process 543, the fractured biomass transitions into a gravity clarifier tank 544 where heavier matter (ruptured cell debris/mass) 545 sinks down through the water column as the lighter matter (intracellular products) 546 rises to the surface where it allows an easier harvest. The heavier sinking mass 545 gathers at the bottom of the clarifier tank 544 where it can be easily harvested for other useful substances. After substance separation and recovery, the remainder of the water column 547 is sent through a water reclaiming process and after processing is returned back into the growth containment system 540.

Figure 12:
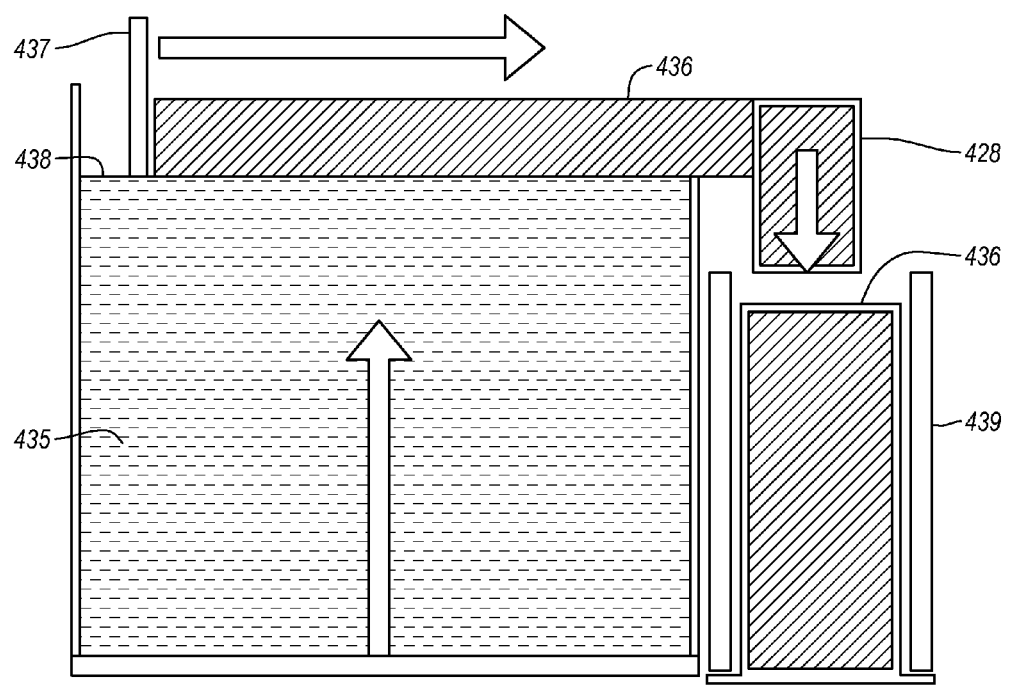
FIG. 12 illustrates a secondary tank containing the liquid medium and a resulting foam layer capable of being skimmed off the surface of the liquid medium, into a foam harvest tank.

FIG. 12 illustrates another embodiment of a method and apparatus (system) as described herein for the harvest of useful substances from an algae biomass. Microorganism algae are grown in a containment system 648 and at the end of an appropriate growth cycle are then transferred into the substance recovery process. The substance recovery consists of the algae biomass being transfered into an optional heat process 649 where the biomass water column is subjected to heat prior to the EMP station 650. After the EMP process, the fractured biomass is then transferred over into a cavitation station 651 where micron bubbles are introduced at a low point in a water column containment tank 652. As the microbubbles rise through the water column, the valuable released bio substances (intracellular products) 653 attach to the rising bubbles which float to the surface of the water column allowing an easier and faster skimming process for substance recovery. After substance recovery, the remainder of the water column is sent through a water reclaiming process 654 and after processing is returned back into the growth system 648.

EXAMPLES

The present invention is further illustrated by the following specific examples. In the experiments described below, *Nanochloropsis oculata* cells were used. The examples are provided for illustration only and should not be construed as limiting the scope of the invention in any way.

Example 1

Cell Lysing Method and Apparatus

In view of the interest in algae as a source of fuels and other materials, the development of methods and apparatuses for processing algal cells on a large scale is of great utility in processing the algal cells for such purposes. Such methods and apparatuses are described below.

One embodiment of a method for processing algal cells in suspension involves passing algal cells in aqueous suspension through a static mixer, where the static mixer creates cavitation effects, electrolyzing the suspension, and separating lysed cells from water in the suspension.

In particular embodiments, the method also involves entraining a pH or ORP modifying agent in the suspension, e.g., carbon dioxide. In such an embodiment, carbon dioxide typically is entrained in a static mixer. In a further refinement, because alkaline materials may assist (make the process more efficient), agents may be used.

In certain embodiments, the method also involves collecting hydrogen gas generated by the electrolysis, e.g., at the mixer.

In certain advantageous embodiments, the suspension is a partial draw from an algal growth container, e.g., a draw taken 1, 2, or 3 times per day, or a draw taken once every 1, 2, 3, 4, 5, 6, or 7 days. Generally, the partial draw consists of approximately 10, 20, 30, 40, 50, 60, 70, 80, or 90 percent of the culture volume from an algal growth container or is in a range of 10 to 30, 30 to 50, 50 to 70, or 70 to 90 percent of the culture volume. Lysed and/or flocculated algal cells are separated from water in the suspension to provide recovered water, and the recovered water is sterilized and returned to the algal growth container.

In another embodiment, a system for processing algal cells in suspension includes a growth container in which algal cells are grown in suspension; a static mixer fluidly connected with the container through which at least part of the suspension is passed, thereby lysing at least some of said cells; and electrolysis electrodes in contact with the suspension, wherein an EMP is passed through the electrodes and through suspension between the electrodes.

In certain embodiments, the static mixer includes an injection port through which fluid may be entrained in the suspension; the static mixer also includes anode and cathode electrodes electrically connected to an electrical power source, e.g., as described herein.

In certain embodiments, the system also includes a biomass separator, a lipid extractor, and/or a hydrogen collector.

Some embodiments include a modified static mixer. Such a modified static mixer includes a body having a mixing throat through which liquid is passed, an injection port whereby fluid materials may be entrained in said liquid, and anode and cathode electrodes electrically separated from each other such that when a voltage is applied across said electrodes, an electrical current will pass through said liquid.

While such a mixer may be configured in many ways, in certain embodiments, one of the electrodes is within the body, and the other of the electrodes is located at the outlet in the body; one of the electrodes consists essentially of the body of the mixer, and the other of the electrodes consists essentially of an outlet ring insulated from the body.

Utilization of algae in methods for producing large quantities of algal oil or algal biomass has faced a number of hurdles. In addition to achieving efficient growth, those hurdles include efficiently separating algae biomass from culture fluid and lysing of cells to enable separation of oils or other products from cellular mass and debris. The problems are dramatically increased in large scale operations in contrast to laboratory scale processes. Indeed, many laboratory scale processes are not applicable to large scale operations due to physical limitations and/or cost limitations.

For example, in investigating these matters, no suggestion has been found for industrial scale application of EMP to the cell lysis of organisms of the taxonomy group: *Archeaplastida* and particularly its sub group micro-algae. Indeed, conventional methods focus mainly on electrolysis of sludge (i.e., municipal and industrial waste) which is lower in pH and therefore has a higher or positive Oxygen Reduction Potential (ORP) or Mv reading.

Electrochemically, as pH lowers, there is a dramatic increase in the concentration of hydrogen ions and a decrease in negative hydroxyls or OH-ions (J. M. Chesworth, T. Stuchbury, J. R. Scaife, Introduction to Agricultural Biochemistry, pg 12. 2.2) Conversely, the higher the pH, the lower the ORP. This correlation between high pH and negative Mv readings led to the conclusion that a resident charge on the cell wall can be transformed as energy to both facilitate cell lysing, but also to extract desired elements within the cell of benefit for the production of energy, pharmaceuticals and food products.

From recent advances in X-ray crystallography biology of single cell organism, in this case cyanobacteria or blue green algae, it was concluded that plant cell membranes are like the two ends of a battery, they are positive on the inside and negative on the outside, and they are charged up when solar energy excites electrons from hydrogen within the cell. The electrons travel up into the cell membrane via proteins that conduct them just like wires releasing the energy a plant needs to stay alive and from data on the accumulation of tetraphenylphosphonium within *Chlorella vulgaris* cells, it can be estimated that these cells possess a membrane potential of −120 to −150 mV.

This negative potential is reflected in the observation of a vibrant cell colony's matrix pH level, where this measurement along with the correlate ORP (Mv reading) were taken to determine cell colony health. For example, a pH reading of 7 in an algae growth vessel correlate to an ORP reading of (+/−)+200 Mv. When good cell health or log growth is attained; the pH of the matrix was noted to be pH 9.0; the corollary ORP reading was (+/−)−200 Mv. Therefore, it can be surmised that the measure of a healthy algae cell colony can be determined by a negative Mv reading with each increase in one point of pH correlating to a decrease of roughly 200 Mv.

Most natural waters have pH values of between 5.0 and 8.5. As plants take in $CO_2$ for photosynthesis in aquatic ecosystems, pH values (and alkalinity) rise. Aquatic animals produce the opposite effect—as animals take in $O_2$ and give off $CO_2$, the pH (and acidity) is lowered. In steady state, the algae matrix reading was 7.0 pH and as hypertonic conditions are created through oxidation, the pH drops to below 7.0 and as low as 5.0 with an analogous ORP reading of +200 to +400 Mv. When the cell wall does not collapse, but just becomes flaccid (as opposed to turgid); its contents are still encysted and the cell wall as represented in Donnan's law of equilibrium where the cell wall sets up an energy potential within its two opposite charged cell walls to survive until an isotonic state is regained. This is also referred to as the Gibbs-Donnan phenomenon. This is the state of equilibrium existing at a semipermeable membrane when it separates two solutions containing electrolytes, the ions of some of which are able to permeate the membrane and the others not; the distribution of the ions in the two solutions becomes complicated so that an electrical potential develops between the two sides of the membrane and the two solutions have different osmotic pressures. This charge is extremely balanced and is why cells can survive extreme adverse conditions only to rejuvenate when proper hypotonic conditions are present.

Live algal cells can be considered as an electrochemical fuel cell, where changing the polarity of the membrane from a live culture high pH and low ORP (150 Mv) to a low pH and high ORP (+200 Mv) results in the net gain of 350 Mv and an attendant release of hydrogen into the matrix, provided the electrical potential of the cell is broken and the cell wall is not just deflated. Such hydrogen production is one of the beneficial products obtainable from this invention.

By combining a number of approaches, it was discovered that a rapid, industrially scalable method of lysing and/or flocculating algal cells can be provided. Such methods can be applied in methods for obtaining useful products from algae, for example, extracting lipids, obtaining hydrogen gas, and/or obtaining algal cellular mass and debris, among others As a component to carry out such a process, the present methods can use a static mixer. Advantageous static mixers include but are not limited to those described in Uematsu et al., U.S. Pat. No. 6,279,611, Mazzei, U.S. Pat. No. 6,730,214.

Such mixers that assist in the generation of transient cavitation and/or mass transfer of gas to liquid can be used.

It is surmised that by creating a rapid increase in ORP through manipulation or lowering the pH of the matrix, the electrical differential has the effect of abetting the electrolysis process in cell lysing with the attendant benefit of the generation of excess hydrogen as a byproduct of the cell wall content release.

Experimental work demonstrates that cell lysing was realized rapidly and economically with this combination. The theory of why a combination of cavitation, ultrasonics and pH modification works to lyse cells is empirical and the inventors are not intending to be bound by any particular explanation of the results.

The present process can advantageously include modification of ORP, usually through pH reduction. While such pH reduction (or other ORP modification) can be accomplished using a variety of acids and bases, it can also be accomplished using $CO_2$. Oxidation/reduction reactions involve an exchange of electrons between two atoms. The atom that loses an electron in the process is said to be "oxidized." The one that gains an electron is said to be "reduced." In picking up that extra electron, it loses the electrical energy that makes it "hungry" for more electrons. Chemicals like chlorine, bromine, and ozone are all oxidizers.

ORP is typically measured by measuring electrical potential or voltage generated when a metal is placed in water in the presence of oxidizing and reducing agents. These voltages give us an indication of the ability of the oxidizers in the water to keep it free from contaminants. Thus, an ORP probe is really a millivolt meter, measuring the voltage across a circuit formed by a reference electrode constructed of silver wire (in effect, the negative pole of the circuit), and a measuring electrode constructed of a platinum band (the positive pole), with the fluid being measured in between. The reference electrode, usually made of silver, is surrounded by salt (electrolyte) solution that produces another tiny voltage. But the voltage produced by the reference electrode is constant and stable, so it forms a reference against which the voltage generated by the platinum measuring electrode and the oxidizers in the water may be compared. The difference in voltage between the two electrodes is measured.

Changing the pH of an aqueous solution can dramatically alter the ORP reading because of the effect of pH on the concentration of charged ions in the water. Thus, in the apparatuses and methods described herein, the pH and thus the ORP can be modified by contacting the water with one or more ORP or pH modifying agents. Advantageously, carbon dioxide gas can be used to lower the pH; bringing the pH down will raise the millivolt reading.

$CO_2$ can be entrained in the liquid medium in the form of micro or nanobubbles, e.g., entrained as micro or nanobubbles using a static mixer as described above. Entrainment of $CO_2$ gas in such a manner lowers the pH, modifying the ORP, which can lead to the production of additional hydrogen gas which can be collected.

In addition, entrainment of $CO_2$ (or other gas) as micro or nanobubbles can contribute to cell lysis as indicated below. Cavitation effects and/or ultrasonics can also be beneficially utilized to enhance cell lysis and/or cellular mass and debris flocculation. While such effects can be generated using an ultrasonic probe, they can also be generated using the cavitation effect of a static mixer with associated microbubble entrainment. Thus, passing the algae-containing medium through a static mixer with gas entrainment contributes to cell rupture and can assist cellular mass and debris flocculation.

As applied in the present system, EMP has the effect of lysing cells. However, an added benefit is the generation of hydrogen gas, which can be collected, e.g., for use as a fuel. The quantity of hydrogen can be enhanced by ORP modification.

For some applications, it may also be beneficial to apply a magnetic field. For example, such a field can be applied in or adjacent to a static mixer. One way of accomplishing this is to locate strong magnets around the static mixer. In some cases, it may be beneficial to use alternating magnetic fields.

The present process can be configured to enhance the output of one or more of a number of different products. For example, products can be algal cellular mass and debris, lipids, selected proteins, carotenoids, and/or hydrogen gas.

In some applications, it may be desirable to generate cellular mass and debris using the methods and apparatuses described herein. Such cellular mass and debris can be produced in conjunction with enhanced or optimized production of one or more other products, or either without obtaining other products or without optimizing for obtaining other products.

Advantageously, the process can be configured to produce substantial amounts of hydrogen gas.

In a typical embodiment, it is desirable to obtain lipids from the algae, e.g., for use in biofuels and/or to provide algal omega-3 fatty acid containing oils (primarily eicosapentaenoic acid (20:5, n-3; EPA) and docosahexaenoic acid (22:6, n-3; DHA). For extracting such lipids, it is advantageous to lyse the cells, e.g., as described above. Release of lipids in such a manner allows a first separation to be carried out on the basis of different densities between the lipid-containing material and the bulk water. If desired, the lipids can be further extracted using other lipid extraction methods.

In some embodiments, this invention utilizes a plurality of the processes mentioned to produce enhanced cellular mass and debris separation, cell lysis, hydrogen production, and/or lipid separation. For example, electrolysis can be combined with ORP modification.

Highly advantageously, a system is constructed to carry out the selected sub-processes as part of the overall algae processing method. One component useful in such a system utilizes a modified static mixer which has an anode and cathode built into the device. In use, the modified static mixer subjects the slurry to EMP, while concurrently injecting $CO_2$ gas or other ORP modifying agent through a venturi into the algae liquor as it flows through the device. The device can include a gas recovery system on either end for the recovery of gases (e.g., hydrogen) generated by the electrolysis process.

Figure 15:
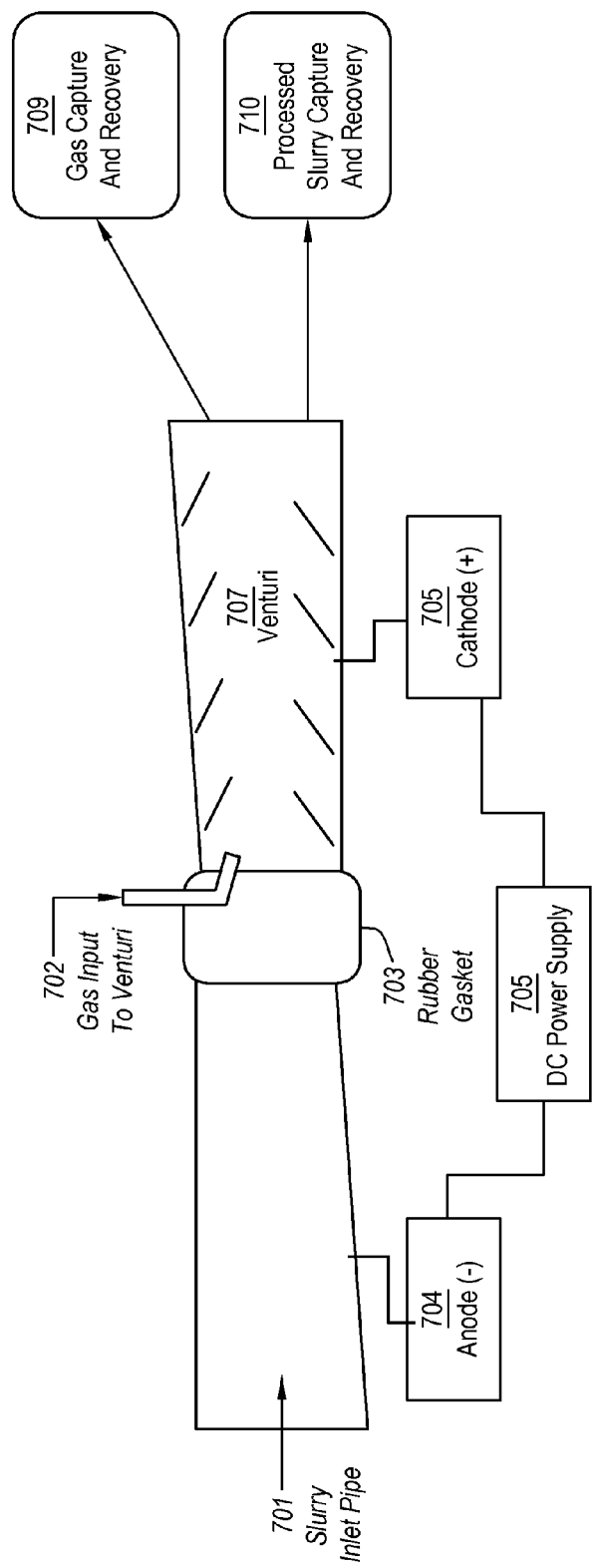
FIG. 15 illustrates an example of a modified static mixer.

Such a modified static mixer is schematically illustrated in FIG. 15. Biomass slurry 601 is allowed entry into the mixer chamber via an intake pipe. Once inside the entry chamber the slurry 601 flows through an anode 602 and cathode 603 circuits which is powered by a direct current power supply 654. The anode and cathode electrodes, 602 and 603, only allow electrical transfers when a conductive liquid medium is flowed between them. In the case of this static mixer, the biomass slurry 601 is used to conduct the electrical transfer between the anode and cathode electrodes, 602 and 603. During electrical transfer, the biomass slurry 601 is further exposed to the transfer and with a partial amount of this transfer absorbed by the microorganism cells. Once electrical exposure occurs their cellular wall structures begin to weaken. After flowing through the anode and cathode circuit chamber, a non-conductive gasket 655 is used to isolate the two chambers apart as so to not allow and electrical transfer to the venturi chamber 656. The now structurally weaker cells can now be fractured by cellular/micron bubble collision caused by the venturi. To further increase efficiency of the substance separation process, a gas injection port 657 can be used to introduce chemical enhancements for substance fracturing and recovery. During cellular wall fracturing, a release of intercellular gases such as oxygen and hydrogen or others having value can be captured as part of the substance recovery system. These gases are directed to vent for capture at the end of the outlet 658 located at the static mixer exit port 659. Further exiting are the remains of the fractured biomass 629 which is also directed for recovery at the exit point 658.

Thus, as indicated above, the system can advantageously be configured and used with partial draws from the growth container or reactor, e.g., a photo bioreactor. Also advantageously, the system can include and use a modified static mixer as described for extracting and flocculating (cellular mass and debris) from the matrix, capturing the generated hydrogen or excess oxygen, separating the cellular mass and debris from the water and returning the water back to the reactor, preferably after sterilization or filtration.

The method referred to herein as "Cascading Production", makes use of a percentage draw of (culture) liquor from the growth tank on a scheduled basis such as daily, every other day or weekly. The drawn (culture) liquor is then entrained through the electrolyzing mixing device and/or entrained through a mixer in conjunction with conventional electrolyzing method, such as an anode and cathode plate in the processing tank. Such processing can include ORP manipulation.

Viewed in a general sense, the methods and apparatuses described herein include a series of fluid manipulations along a process flow with the specific goal of extracting valuable by-products contained in algal cells. As described briefly above, as the algae is grown in tanks, e.g., salt water tanks, of diverse configurations such as outdoor growth ponds, open tanks, covered tanks, or photo bioreactors (PBR), a portion of the solution or liquor is drawn on a scheduled basis. This draw schedule is determined but not limited to the following observations taken on a daily basis of density, pH and/or ORP. For example, it has been noted that the pH of an outdoor pond is higher in the evening than during the morning, due to $CO_2$ absorption and the process referred to as respiration which occurs at night. The difference can be as high as 3 pH points or 600 Mv. Therefore, one would draw a significant portion of the growth pond in the evening as the pH is now at 8.5-10 (early morning readings would compare at (6.-7). In a reactor or PBR, the same principle applies, but in this case one observes the log stages of growth and draws up to 75% of the growth fluid (matrix) when the pH reaches 8.5-9. All these indicators use conventional measuring equipment incorporated into a plant process computer controller, that would control the extraction process and signal when it is time to harvest. To determine when it is time to harvest, several indicators in the growth vessel, such as PH, ORP, Mv, salinity, size of cells, etc., can be evaluated.

The remaining percentage of undrawn fluid is kept as an incubator for the recycled water and used to start a new log phase of algae growth. The drawn liquor (also referred to herein as "culture").

Microorganism algae are grown in a containment system and at the end of an appropriate growth cycle are transferred into the substance recovery process. The algae biomass are flowed through an optional micron bubble cavitation step, used to soften the outer cellular wall structure prior to other bio substance recovery processes.

After the cavitation step an optional heat process can be applied to change the gravity specifies of the liquid feed stock water containing the biomass. The heat option allows a faster transfer of particular substances released during the harvest process. After the biomass has reached an appropriate heat range, it is then allowed to flow through an electromagnetic pulse field, the EMP station where transiting biomass cells are exposed to the electromagnetic transfers resulting in the fracturing of the outer cellular wall structures.

Once flowed through the EMP process, the fractured biomass transitions into a gravity clarifier tank where heavier matter (cellular mass and debris) sinks down through the water column as the lighter matter rises to the surface where it allows an easier harvest. The heavier sinking material (cellular mass and debris) gathers at the bottom of the clarifier tank where it can be easily harvested for other useful substances. After substance separation and recovery, the remainder of the water column is sent through a water reclaiming process and after processing is returned back into the growth system.

During this period of "cracking", the static mixer can inject one or more ORP modifiers, which can be or include pH modifiers such as $CO_2$. While $CO_2$ is preferred, alternative or additional pH or ORP modifiers can be used which accomplish the basic function of altering the pH value and its corollary ORP value as represented in Mv. Any suitable static mixer can be used; the methods, systems and apparatuses described herein are not limited to any particular type of mixer or the associated electrolyzing method. Such a mixer can incorporate a cathode and anode connected to a voltage regulator, which preferably flips polarities so as to reduce scaling on the probes. The anode and cathode are powered by a DC energy source, such as a battery, generator, transformer or combination thereof. The DC voltage can be set to variable outputs to adjust to algae mass in the cracking tank.

As the fluid is entrained through the Venturi mixer, it is therefore admixed with $CO_2$, subjected to EMP field as mentioned above, and through the continuous mixing, a plurality of micron bubbles are generated, creating a cavitated, or slurry of micron bubbles of both $CO_2$ and alga mass. A combination of $CO_2$ entrainment, electrolysis, and mixing can be empirically selected, e.g., based on the desired separation of products from the algae cells and/or flocculation of the mass to the surface of the water.

For example, in a recent test, $CO_2$ was applied to attain a drop from pH 8.5 to 6.5 with a corresponding increase from −200 Mv to +250 Mv and the fluid was electrolyzed using a DC 6 Volts power supply and complete flocculation and cell lysing (as examined under a microscope) was obtained within a period of 20 minutes. However, this combination and these parameters are only exemplary, and can be examined to determine optimum values. Desired results can be further correlated with processing variables, e.g., to establish protocols based on pH values, ORP reading, cell density and alga species. Upstream PH modification, prior to extraction, may help the emf extraction process.

When electrolysis is utilized, concurrent with the process of cracking (lysing) hydrogen gas (H+) is released at the cathode. This hydrogen can be safely recovered and trapped in a tank through a hydrogen recovery valve, placed on the cathode end of an electrolyzing unit or at the end of the static mixer. If one alters the pH values by using a base chemical compound, e.g., potassium hydroxide, sodium hydroxide, calcium hydroxide or magnesium hydroxide, one would now create an excess of free oxygen at the anode probe. In this instance, one would draw as above a certain portion of algae mass at a pH value of 8.5 and raise that value to approximately pH 11 or roughly −250 Mv to −700 Mv and create a matrix high in negative hydroxyls or —OH. The dissociation of the free oxygen would then be created as the matrix returned to 7.0 upon cell cracking. In this case, one would incorporate a safe recovery system for this oxygen.

In this system, once the cellular mass and debris is cracked, depending on the conditions, it may flocculate to the surface of the water or may sink. The cellular mass and debris is generally a composite of broken cell wall, lipid, carbohydrate and chlorophyll (A). In many cases, within a few hours, floc at the surface sinks to the bottom of the tank. While some of the lipid may remain on the surface, a significant fraction of the lipid (which may be most of the lipid) is still associated with chlorophyll and/or other cellular components and will sink with the rest of the cellular mass and debris.

The remainder of the water is now of about 7.0 pH, with a high $CO_2$ concentration. (only if pH was adjusted, otherwise the PH will be that of the inbound slurry) This water (slurry is processed) and its cracked biomass (cellular mass and debris) is now entrained or flowed to a water sterilizing tank after passing through a filtration unit, where a number of systems can be used to separate out the organic mass from the water. These systems can, for example, be plane separators, filters, vortex separators or any other method that performs the function of delivering a separated mass. The separated cellular mass and debris is drawn to a cellular mass and debris collection vessel and the water is sent on for sterilization in tank. After sterilization, the recovered water can be used to replenish tank.

Figure 13:
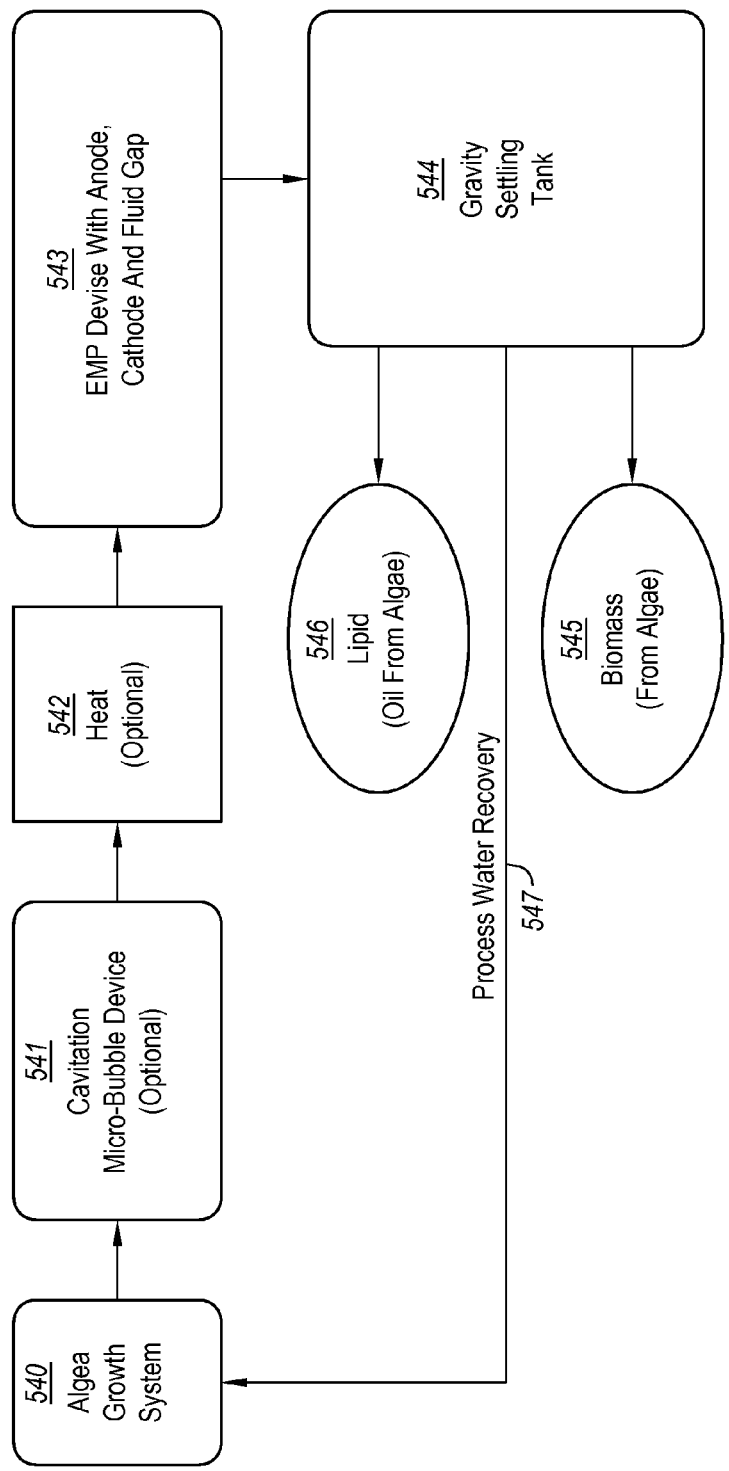
FIG. 13 illustrates one embodiment of a method and apparatus (system) as described herein for the harvest of useful substances from an algae biomass involving extraction with an emf.

In one embodiment, the system includes a modified Venturi mixer nozzle, e.g., as illustrated in FIG. 13. As previously indicated, the slurry input pipe is insulated in the middle, or anywhere else along the length of pipe with a large rubber gasket or other electrically insulating material so as to separate the polarity of the anode and cathode. The two ends of the tube can be electrified from source DC input or include probes within the tubes that have the purpose of conducting electricity. The modified Venturi introduces $CO_2$ gas or other admixture with the purpose of altering pH and ORP through an inlet tube into a low pressure zone designed within the geometry of the tube; according to Bernoulli's principle. At the exit of the venturi tube, a device can be installed for the purpose of capturing the hydrogen created during the EMP process. One can add obstructions within the venturi tube to impact the fluids flow to increase turbulence and create a plurality of micron-bubbles.

Example 2

Quantification of Lipid Extraction and Identification of Optimal EMP Extraction Parameters In the experiments described below, quantification of lipid extraction using an EMP apparatus as described herein and identification of optimal extraction parameters are described. The results described below correspond to the data in FIG. 16.

Test 1:
In order to quantify lipid extraction from an EMP unit as described herein, the following experiment was performed. A batch of *Nannochloropsis oculata* was processed through the 6-inch EMP unit to extract the lipids. The batch was gravity fed through the EMP unit at a flow rate of about 1 L/min. A total of 20.8 L of algae culture was processed. The processed stream was scooped off the top layer after collection for lipid analysis.
Control Batch Details:
Dry mass concentration: 433 mg/L
Lipid content: 5.5% of dry mass (23.86 mg/L)
pH: 7.1
Conductivity: 8.82 mS/cm
Extraction Process Details:
Extraction sample volume: 20.8 L
Flow rate: 1 L/min
Voltage: 4.3 V
Electric current: 22 Amp
Results: The extraction sample was analyzed by the Folch method. The extracted lipid weighed 0.4481 g. The amount of lipid originally present in the 20.8 L of algae batch before processing was 0.4965 g. This corresponds to an extraction efficiency of 90.2% through the EMP unit.

Test 2:
In order to quantify lipid extraction from an EMP unit as described herein, the following experiment was performed. A batch of *Nannochloropsis oculata* was processed through the 6-inch EMP unit to extract the lipids. The batch was gravity fed through the EMP unit at a flow rate of about 1 L/min. A total of 9.2 L of algae culture was processed. The processed stream was collected in a lipid collection apparatus that was designed to have tapered long neck to collect the lipid layer floating at the top.
Control Batch Details:
Dry mass concentration: 207 mg/L
Lipid content: 13% of dry mass (26.91 mg/L)
pH: 6.8
Conductivity: 9.31 mS/cm
Extraction Process Details:
Extraction sample volume: 9.2 L
Flow rate: 1 L/min
Voltage: 3.4 V
Electric current: 20 Amp
Results: The extraction sample was analyzed by the Folch method. The extracted lipid weighed 0.2184 g. The amount of lipid originally present in the 9.2 L of algae batch before processing was 0.2477 g. This corresponds to an extraction efficiency of 88.2% through the EMP unit.

Test 3
In order to quantify lipid extraction from an EMP unit as described herein, the following experiment was performed. A batch of *Nannochloropsis oculata* was processed through the 6-inch EMP unit to extract the lipids. The batch was gravity fed through the EMP unit at a flow rate of about 1 L/min. A total of 11 L of algae culture was processed. The processed stream was scooped off the top layer after collection for lipid analysis.
Control Batch Details:
Dry mass concentration: 207 mg/L
Lipid content: 13% of dry mass (26.91 mg/L)
pH: 6.8
Conductivity: 9.31 mS/cm
Extraction Process Details:
Extraction sample volume: 11 L
Flow rate: 1 L/min
Voltage: 3.4 V
Electric current: 20 Amp
Results: The extraction efficiency was 95.25% through the 6-inch EMP unit for the tested algae batch.

Test 4
In order to quantify lipid extraction from an EMP unit as described herein, the following experiment was performed. A batch of *Nannochloropsis oculata* was processed through the 6-inch EMP unit to extract the lipids. The batch flow rate was regulated using a flowmeter and a pump. 2 liters of algae culture was processed. The processed stream was collected in a 2 liter volumetric flask, and the top lipid layer was recovered for analysis.

Control Batch Details:
Dry mass concentration: 410 mg/L
Lipid content: 8.2% of dry mass (33.62 mg/L)
pH: 7.1
Conductivity: 8.99 mS/cm
Extraction Process Details:
Extraction sample volume: 2.01 L
Flow rate: 1.5 L/min
Voltage: 12.4 V
Electric current: 18 Amp
    Results: The extraction efficiency was 90.7% through the 6-inch EMP unit for the tested algae batch.
Test 5
    In order to quantify lipid extraction from an EMP unit as described herein, the following experiment was performed. A batch of *Nannochloropsis oculata* was processed through the 12-inch EMP unit to extract the lipids. The batch flow rate was regulated using a flowmeter and a pump. 1.87 liters of algae culture was processed. The processed stream was collected in a 2 liter volumetric flask, and the top lipid layer was recovered for analysis.
Control Batch Details:
Dry mass concentration: 800 mg/L
Lipid content: 19.9% of dry mass (159.2 mg/L)
pH: 7.6
Conductivity: 8.15 mS/cm
Extraction Process Details:
Extraction sample volume: 1.87 L
Flow rate: 1.13 L/min
Voltage: 4.7 V
Electric current: 20 Amp
    Results: The extraction efficiency was 51.5% through the 12-inch EMP unit for the tested algae batch.
Test 7:
    In order to identify the optimal EMP extraction parameters for a given algae batch, the EMP was tested in a matrix of wide range of parameters. A batch of *Nannochloropsis oculata* was processed through the 6-inch EMP unit to extract the lipids. The batch flow rate was regulated using a flowmeter and a pump. Individual samples that comprised the matrix of testing were collected in small 116 ml bottles. The cellular mass and debris at the bottom and the water were syringed out leaving only the top lipid layer in the extraction sample bottle.
Control Batch Details:
Dry mass concentration: 210 mg/L
Lipid content: 24% of dry mass (50 mg/L)
pH: 7.8
Conductivity: 7.89 mS/cm
Extraction Results:
Extraction sample volume: 116 ml
    The amount of lipid originally present in the 116 ml algae sample before processing: 5.8 mg The extraction sample was analyzed by the Folch method. The relevant parameters comprising the matrix of testing conditions and the extraction efficiency are tabulated in Table 1.

TABLE 1

Extraction efficiency at different flow rates and current strengths

| Flow rate | Current | | | |
|---|---|---|---|---|
| | 5 Amp | 10 Amp | 15 Amp | 20 Amp |
| 0.25 gal/min (0.95 L/min) | Sample # 2<br>Voltage: 11.5 V<br>Lipid extracted: 4.0 mg<br>Efficiency: 69% | Sample # 5<br>Voltage: 11.5 V<br>Lipid extracted: 4.2 mg<br>Efficiency: 72% | Sample # 8<br>Voltage: 11.5 V<br>Lipid extracted: 5.6 mg<br>Efficiency: 97% | Sample # 10<br>Voltage: 11.5 V<br>Lipid extracted: 5.2 mg<br>Efficiency: 90% |
| 0.38 gal/min (1.44 L/min) | Sample # 14<br>Voltage: 11.5 V<br>Lipid extracted: 3.0 mg<br>Efficiency: 52% | Sample # 17<br>Voltage: 11.5 V<br>Lipid extracted: 4.5 mg<br>Efficiency: 78% | Sample # 20<br>Voltage: 11.5 V<br>Lipid extracted: 4.1 mg<br>Efficiency: 71% | Sample # 23<br>Voltage: 11.5 V<br>Lipid extracted: 4.5 mg<br>Efficiency: 78% |
| 0.5 gal/min (1.89 L/min) | Sample # 26<br>Voltage: 11.5 V<br>Lipid extracted: 3.3 mg<br>Efficiency: 57% | Sample # 29<br>Voltage: 11.5 V<br>Lipid extracted: 3.2 mg<br>Efficiency: 55% | Sample # 32<br>Voltage: 11.5 V<br>Lipid extracted: 3.0 mg<br>Efficiency: 52% | Sample # 35<br>Voltage: 11.5 V<br>Lipid extracted: 2.6 mg<br>Efficiency: 45% |

Flow rate: 0.2 gal/min (0.756 L/min)
Voltage: 4.8 V
Electric current: 20.2 Amp
    Results: The extraction efficiency was 12.2% through the 12-inch EMP unit for the tested algae batch.
Test 6:
    In order to quantify lipid extraction from an EMP unit as described herein, the following experiment was performed. A batch of *Nannochloropsis oculata* was processed through the 12-inch EMP unit to extract the lipids. The batch flow rate was regulated using a flowmeter and a pump. 1.87 liters of algae culture was processed. The processed stream was collected in a 2 liter volumetric flask, and the top lipid layer was recovered for analysis.
Control Batch Details:
Dry mass concentration: 500 mg/L
Lipid content: 16.15% of dry mass (80.75 mg/L)
pH: 7.5
Conductivity: 8.18 mS/cm Inference: The most optimal conditions for lipid extraction for this batch of algae look to be 0.25 gal/min and 15 Amp. The efficiency decreases gradually around this set of conditions in the tested matrix. At higher currents at 0.25 gal/min, the energy input is probably too high to the detriment of algae causing them to destruct. At lower currents at 0.25 gal/min, and at lower flow rates, the energy input is too less to fully extract the lipids from algae.
Test 8:
    In order to quantify lipid extraction from an EMP unit as described herein, the following experiment was performed. A batch of *Nannochloropsis oculata* was processed through the 6-inch EMP unit to extract the lipids. The batch flow rate was regulated using a flowmeter and a pump. Samples were collected either in 116 ml bottles or 400 ml bottles. The cellular mass and debris at the bottom and the water were syringed out leaving only the top lipid layer in the extraction sample bottles.

Control Batch Details:
Dry mass concentration: 320 mg/L
Lipid content: 18% of dry mass (57.6 mg/L)
pH: 7.3
Conductivity: 7.93 mS/cm
Extraction Process Details:
Flow rate: 0.95 L/min
Voltage: 5.3 V
Current: 20 A
Results:
Extraction sample 1:
Volume: 412 ml
Extraction efficiency: 83.31%
Extraction sample 2:
Volume: 116 ml
Extraction efficiency: 80.69%
Extraction sample 3:
Volume: 116 ml
Extraction efficiency: 95.64%

Test 9:

In order to identify the optimal EMP extraction parameters for a given algae batch, the EMP apparatus as described herein was tested in four different sets of conditions. 20 liters of a *Nannochloropsis oculata* batch from the grow room was processed through the 6-inch EMP unit. The batch flow rate was regulated using a flowmeter and a pump.

Control Sample Details (Sample #1130-0):
Dry mass concentration: 320 mg/L
Lipid content: 11% of dry mass (35 mg/L)
pH: 7.5
Conductivity: 8.15 mS/cm The algae batch was processed under various flow rate and energy input conditions as listed below:
Sample 1130-3: Flow rate=0.25 gal/min, Voltage=3.7 V, Current=15 Amp
Sample 1130-4: Flow rate=0.25 gal/min, Voltage=4.0 V, Current=20 Amp
Sample 1130-8,9: Flow rate=0.38 gal/min, Voltage=4.0 V, Current=20 Amp
Sample 1130-12: Flow rate=0.38 gal/min, Voltage=3.7 V, Current=15 Amp Samples were collected in 400 ml bottles. The cellular mass and debris at the bottom and the water were syringed out leaving only the top lipid layer in the extraction sample bottles. The samples were analyzed by CSULB-IIRMES using the Folch Method.

Results: The most optimal conditions for lipid extraction for this batch of algae look to be 0.38 gal/min; 3.7 V; 15 Amp.

TABLE 2

| Sample # | Extraction Sample Volume (L) | Lipid Content Before Extraction (mg/L) | Lipid Extracted (mg/L) | Extraction Efficiency |
|---|---|---|---|---|
| 1130-3 | 0.38 | 35 | 25.3 | 72% |
| 1130-4 | 0.38 | 35 | 27.9 | 80% |
| 1130-8,9 | 0.38 | 35 | 26.8 | 77% |
| 1130-12 | 0.38 | 35 | 32.6 | 93% |

Test 10:

The new Pipe EMP (i.e., pulsed emf) equipment along with MX cavitation and heat was tested and compared with previous tests. A batch of *Nannochloropsis oculata* was processed through the Pipe single step extraction (herein "SSE") system. The components of the Pipe SSE system are the pipe EMP unit, a heat strip system around the pipe EMP unit, and an MX cavitation unit. The MX cavitation unit precedes the pipe EMP unit. The MX cavitation unit and the heating system around the EMP unit could be used optionally. The cavitation was done for 1 minute. The batch flow rate was regulated using a flowmeter and a pump. Samples were collected in 120 ml bottles. The cellular mass and debris at the bottom and the water were syringed out leaving only the top lipid layer in the extraction sample bottles.

Control Batch Details:
Dry mass concentration: 280 mg/L
Lipid content: 21% of dry mass
pH: 7.7
Conductivity: 7.42 mS/cm
Extraction Results and Observations:
Extraction sample volume: 120 ml

TABLE 3

Extraction results and observations of the Pipe SSE testing that included both MX cavitation and heating

| Current (Amp) | Flow rate (gal/min) | | | |
|---|---|---|---|---|
| | 0.25 | 0.50 | 1.00 | 2.00 |
| 5 | Voltage = 2.1 V cellular mass and debris sank after 60 min | Voltage = 2.1 V All cellular mass and debris floated | | |
| 10 | Voltage = 3.1 V cellular mass and debris sank after 25 min | | | |
| 15 | Voltage = 2.6 V cellular mass and debris sank instantly Extraction Efficiency = 66% | Voltage = 2.6 V All cellular mass and debris floated Extraction Efficiency = 65% | Voltage = 2.6 V All cellular mass and debris floated | Voltage = 2.6 V All cellular mass and debris floated |
| 20 | Voltage = 3.8 V cellular mass and debris sank instantly | Voltage = 3.8 V cellular mass and debris sank slowly (1 day) | | |

Note:
Rate of heating was the same for different flow rates. This means that at 0.50 gal/min, cellular mass and debris received less heat than that at 0.25 gal/min The following table (Table 4) shows the extraction results and observations of the Pipe EMP testing that included only of MX cavitation and heating or neither. This can be used for comparison with the similar testing conditions in the table above.

TABLE 4

Extraction Results

|  | 0.50 gal/min; 15 Amp | 1.00 gal/min; 15 Amp |
|---|---|---|
| No MX/No Heat | Voltage = 3.5 V<br>cellular mass and debris was suspended<br>Extraction Efficiency = 95% | Voltage = 3.5 V<br>cellular mass and debris was suspended |
| No MX/Heat | Voltage = 2.5 V<br>All cellular mass and debris floated<br>Extraction Efficiency = 107% | Voltage = 2.5 V<br>All cellular mass and debris floated |
| MX/No Heat | Voltage = 3.6 V<br>cellular mass and debris was suspended<br>Extraction Efficiency = 50% | Voltage = 3.6 V<br>cellular mass and debris was suspended |

It looked like heat resulted in enhanced electrolysis that resulted in the cellular mass and debris to flocculate better. When the heat was high (as in @ 0.25 gal/min), all the flocculated cellular mass and debris sunk leaving a clear thin lipid layer at the top. The sinking was probably because the density of heated water is markedly lower than that of cellular mass and debris. When the heat is low (as in @ 0.50 gal/min), all the flocculated cellular mass and debris remained at the top stuck to the lipid. This is probably because the differential densities of water and cellular mass and debris is not big enough to cause instant sinking of cellular mass and debris, but the applied heat was still enough to flocculate the cellular mass and debris. Either way, it was seen that when there was heat the cellular mass and debris flocculated either at the top or at the bottom, but when there was no heat they remained suspended as seen normally with the previous 6-inch and 12-inch EMP units without heat.

Another strong possibility is that when the cellular mass and debris flocculates and sinks to the bottom with the application of heat, some of the extracted lipid that was stuck to the cellular mass and debris could be carried along with the cellular mass and debris to the bottom. As a result, the extraction efficiency as analyzed from the lipid at the top clear layer could be lower. Conversely, when the cellular mass and debris flocculated and floated at the top, even if all of the lipids inside the algae cells may not have been extracted, the non-extracted lipids may still remain at the top along with the extracted lipids.

Another observation was the effect of current in sinking the cellular mass and debris when heat was applied. In the first table, in the column corresponding to 0.25 gal/min, the speed at which the cellular mass and debris sank was directly proportional to the amount of electric current supplied. Even at the flow rate 0.50 gal/min, where all the cellular mass and debris floated because of lower heat, the cellular mass and debris corresponding to the sample with 20 Amperes of electric current sank after 1 day, whereas the cellular mass and debris corresponding to the samples with lower current continued to float after 1 day.

Test 11:

In order to obtain lipid extraction at the highest efficiency possible for a given batch of algae, an EMP apparatus as described herein was tested in different sets of conditions. A batch of *Nannochloropsis oculata* was processed through the 6-inch EMP unit to extract the lipids. The batch flow rate was regulated using a flowmeter and a pump. Samples were collected in 1 liter bottles. The cellular mass and debris at the bottom and the water were syringed out leaving only the top lipid layer in the extraction sample bottles.

Control Sample Details (Sample #20100104-10):
Dry mass concentration: 285 mg/L
Lipid content: 6.67% of dry mass (19 mg/L)
pH: 8.4
Conductivity: 7.99 mS/cm
Extraction Results:
Extraction sample volume: 1 L
The amount of lipid originally present in the 1 L algae sample before processing: 19 mg The samples were analyzed by CSULB-IIRMES using the Folch Method. The relevant parameters of different testing conditions and the extraction efficiencies are tabulated in following table.

TABLE 5

Parameters of Testing Conditions and Extraction Efficiencies

| Flow rate: 0.25 gal/min (0.945 L/min) | Flow rate: 0.50 gal/min (1.89 L/min) |
|---|---|
| Sample # 20100104-11<br>Current: 12 Amp<br>Voltage: 3.5 V<br>Extraction efficiency: 45% | Sample # 20100104-16<br>Current: 20 Amp<br>Voltage: 3.9 V<br>Extraction efficiency: 67% |
| Sample # 20100104-12<br>Current: 14 Amp<br>Voltage: 3.7 V<br>Extraction efficiency: 31% | Sample # 20100104-17<br>Current: 18 Amp<br>Voltage: 3.8 V<br>Extraction efficiency: 96% |
| Sample # 20100104-13<br>Current: 15 Amp<br>Voltage: 3.7 V<br>Extraction efficiency: 39% | Sample # 20100104-18<br>Current: 15 Amp<br>Voltage: 3.7 V<br>Extraction efficiency: 69% |
| Sample # 20100104-14<br>Current: 20 Amp<br>Voltage: 4.0 V<br>Extraction efficiency: 41% | |
| Sample # 20100104-15<br>Current: 19 Amp<br>Voltage: 3.9 V<br>Extraction efficiency: 98% | |

The highest extraction efficiencies 98% and 96% were obtained at 0.25 gal/min; 19 Amp; 3.9 V and at 0.50 gal/min; 18 Amp; 3.8 V for the tested algae batch.

Tests 12 and 13:

The effect of overnight storing in darkness and cold on lipid extraction efficiency was examined. Samples from the same algae batch were tested in Test 12 and were tested on the following day in Test 13. The same algae batch tested in Test 12 was tested on the following day (the same tests were run on the same original algae culture; one test occurred on the day the live sample was drawn from the growth tank, i.e., real-time, and the $2^{nd}$ day the remainder of the sample was tested after it rested overnight). A batch of *Nannochloropsis oculata* was processed through the Pipe SSE system. The components of the Pipe SSE system are the pipe EMP unit, a heat strip system around the pipe EMP unit, and an MX cavitation unit. The MX cavitation unit precedes the pipe EMP unit. The MX cavitation unit and the heating system around the EMP unit could be used optionally. The cavitation was done for 1 minute. The batch flow rate was regulated using a flowmeter and a pump. Samples were collected in 120 ml bottles. The cellular mass and debris at the bottom and the water were syringed out leaving only the top lipid layer in the extraction sample bottles.

TABLE 6

The control sample details pertaining to the first day and the second day after storage.

| Control Sample- Test 12 | Control Sample- Following day |
|---|---|
| Dry mass concentration: 255 mg/L | Dry mass concentration: 270 mg/L |
| Lipid content: 15.13% of dry mass (38.57 mg/L) | Lipid content: 14.72% of dry mass (39.74 mg/L) |
| pH: 7.4 | pH: 7.4 |
| Conductivity: 7.64 mS/cm | Conductivity: 7.74 mS/cm |

Extraction Results:
Extraction sample volume: 120 ml

TABLE 7

Relevant parameters of the testing conditions and the extraction efficiencies

| Test 12 (Lipid content of algae in 120 ml: 4.63 mg) | The Following Day (Lipid content of algae in 120 ml: 4.77 mg) |
|---|---|
| Sample # 1, 2 Flow rate: 0.50 gal/min Voltage: 3.8 Current: 15 A MX, No Heat Extraction Efficiency: 16% | |
| Sample # 3, 4 Flow rate: 0.25 gal/min Voltage: 4.1 Current: 19 A No MX, Heat Extraction Efficiency: 19% | |
| Sample # 5, 6 Flow rate: 0.50 gal/min Voltage: 3.8 Current: 15 A No MX, Heat Extraction Efficiency: 23% | Sample # 25, 26 Flow rate: 0.50 gal/min Voltage: 3.8 Current: 15 A No MX, Heat Extraction Efficiency: 20% |
| Sample # 7, 8 Flow rate: 0.50 gal/min Voltage: 3.8 Current: 15 A No MX, No Heat Extraction Efficiency: 45% | Sample # 27, 28 Flow rate: 0.50 gal/min Voltage: 3.8 Current: 15 A No MX, No Heat Extraction Efficiency: 25% |
| Sample # 11, 12 Flow rate: 1.00 gal/min Voltage: 3.7 Current: 12 A MX, Heat Extraction Efficiency: 21% | Sample # 19, 20 Flow rate: 1.00 gal/min Voltage: 3.8 Current: 12 A MX, Heat Extraction Efficiency: 23% |
| Sample # 13, 14 Flow rate: 0.50 gal/min Voltage: 3.8 Current: 15 A MX, Heat Extraction Efficiency: 24% | Sample # 21, 22 Flow rate: 0.50 gal/min Voltage: 3.8 Current: 15 A MX, Heat Extraction Efficiency: 24% |
| Sample # 15, 16 Flow rate: 0.25 gal/min Voltage: 3.8 Current: 15 A MX, Heat Extraction Efficiency: 22% | |

The extraction efficiencies are in general lower than the earlier Pipe SSE experiments. This is probably because the extraction samples were left to sit too long before recovering the top lipid layer. Usually there is some cellular mass and debris that is found in the top lipid layer, but all of it had sunk as a result of letting the samples sit for too long, and along with it some of the lipid could have sunk as well. Comparing the extraction efficiencies observed on the first day and the second day, there does not seem to be any improvement in extraction due to the overnight storage in darkness and cold.

Example 3

Use of Cavitation and EMP to Harvest Carbohydrates and Proteins

Figure 14:
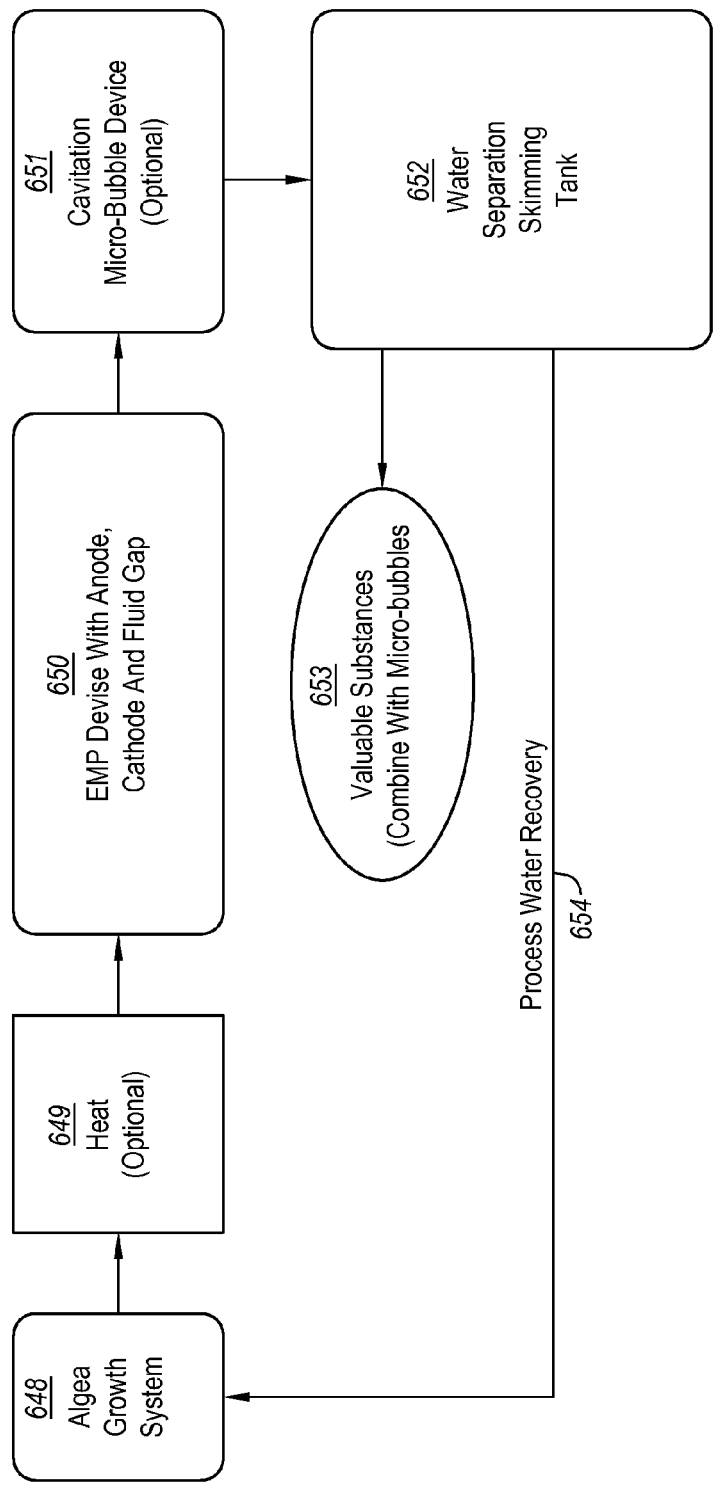
FIG. 14 illustrates another embodiment of a method and apparatus (system) as described herein for the harvest of useful substances from an algae biomass using a lipid extraction device that applies a pulsed emf (i.e. EMP)

FIG. 14 shows results from a test procedure for harvesting carbohydrates and proteins from algae. The test procedure was performed as follows. The algae slurry was first processed through the EMP unit at room temperature. The EMP processed slurry was collected in a storage tank. It was then cavitated through the MX unit. The cavitated slurry was then allowed to sit for a few minutes. A thick mass of algae cellular mass and debris raised to the top and remained floated. The floating cellular mass and debris was collected off the top for analysis.

The algae samples collected through the Inverse SSE process was analyzed by Anresco Laboratories, San Francisco. The samples were analyzed for lipid, protein and carbohydrate content of the algae. The analysis by Anresco Laboratories gave the total mass of protein, lipid or carbohydrate in a given sample (say 'x' mg).

The dry mass concentration of the algae batch processed (say 'd1' mg/L) was measured before the Inverse SSE process. The volume of the algae batch collected in the storage tank from where the final floating cellular mass and debris was collected off the top was also known (say 'V' L). The dry mass concentration of the remnant solution after the collection of floating cellular mass and debris off the top was also measured (say 'd2' mg/L). From these the mass of algae cellular mass and debris (say 'M' mg) collected off the top of the storage tank was calculated as follows:

$$M = (d1 - d2) \times V$$

Then, the individual composition of protein, for example, was calculated as follows:

$$\text{Protein composition} = x/M \text{ mg of protein/mg of algae dry mass.}$$

For this experiment, three small samples were taken from the sample jar (it was observed that the algae collected off the top from the process was sticky, agglomerated and floating on water). Based on the dry mass measurements and the volume of algae slurry processed, the amount of biomass collected off the top through the Inverse SSE process was 600 mg. The protein quantity alone as analyzed by Anresco Laboratories amounts to 1400 mg. As the amount of protein should not be higher than the amount of biomass, the amounts measured could be due to increased protein numbers that resulted from sampling methods, e.g., there might have been more algae in the three drawn samples than there might be if they were uniformly mixed. Nonetheless, these results demonstrate that the apparatuses and methods described herein can be used to harvest protein as well as fat from algae cells (see Table 8 below).

TABLE 8

Results from three samples of Algae marked 0413:1-3

| Sample ID | Analysis | Findings |
|---|---|---|
| #1 | Protein (NX6.25) | 0.70% |
| #2 | Fat | |
| #3 | Fat | |

Other Embodiments

One skilled in the art would readily appreciate that the present invention is well adapted to obtain the ends and advantages mentioned, as well as those inherent therein. The methods, systems, and apparatuses described herein as presently representative of preferred embodiments are exemplary and are not intended as limitations on the scope of the invention. Changes therein and other uses will occur to those skilled in the art, which are encompassed within the spirit of the invention and are defined by the scope of the claims.

It will be readily apparent to one skilled in the art that varying substitutions and modifications may be made to the invention disclosed herein without departing from the scope and spirit of the invention. For example, variations can be made to the configuration of the tanks, materials utilized, ORP modifying agents, and algal species grown. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions, any equivalents of the features shown and described or portions thereof are excluded, but it is recognized that various modifications are possible within the scope of the invention claimed. Thus, it should be understood that although the present invention has been specifically disclosed by exemplary embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values or value range endpoints are provided for embodiments, additional embodiments are described by taking any two different values as the endpoints of a range or by taking two different range endpoints from specified ranges as the endpoints of an additional range. Such ranges are also within the scope of the described invention. Further, specification of a numerical range including values greater than one includes specific description of each integer value within that range.

Thus, additional embodiments are within the scope of the invention and within the following claims.

We claim:

1. A method for extracting non-polar lipids from microalgae in a flowing aqueous slurry, comprising:
   providing an aqueous slurry comprising microalgae;
   providing a lipid extraction apparatus having a body including a channel that defines a fluid flow path, wherein a cathode and an anode form at least a portion of the channel that defines the fluid flow path, the cathode and the anode being spaced apart to form a gap with a distance in a range from 0.5 mm to 200 mm within the channel;
   flowing the aqueous slurry through the channel and applying an electromotive force across the gap that compromises the microalgae cells and releases a lipid fraction having greater than 80 wt % non-polar lipids and less than 20 wt % polar lipids; and
   recovering at least a portion of the nonpolar lipid fraction.

2. A method as in claim 1, wherein the distance across the gap is in a range from 1 mm to 50 mm.

3. A method as in claim 1 or claim 2, wherein the aqueous slurry is caused to flow through the gap at a rate in a range from at least 0.1 ml per second per ml of gap volume to at least 1.0 ml per second per ml of gap volume.

4. A method as in claim 1 or claim 2, wherein the volume of the fluid flow path within the gap is in a range from at least 50 ml to at least 200 ml.

5. A method as in claim 1 or claim 2, wherein at least 70 wt % of microorganism within the aqueous slurry are microalgae.

6. A method as in claim 1 or claim 2, wherein the electromotive force is pulsed at a frequency of at least 1 kHz.

7. A method as in claim 1 or claim 2, wherein the amperage used to create the electromotive force is at least 1 amp and the voltage is in a range from 1V to 1 kV.

8. A method as in claim 1 or claim 2, wherein the channel has a spiral shape and the aqueous algae slurry is caused to flow in a spiral fluid flow path.

9. A method as in claim 1 or claim 2, wherein at least 90 wt % of microorganism within the aqueous slurry are microalgae.

10. A method as in claim 1 or claim 2, wherein the released lipid fraction has a non-polar lipid content in a range from at least 90 wt % to at least 95 wt % and a polar lipid content in a range from less than 10 wt % to less than 5 wt %.

11. A lipid extraction apparatus for extracting non-polar lipids from microalgae, comprising:
   a body including a channel that defines a fluid flow path from a first opening to a second opening, the first opening providing an inlet for an aqueous algae slurry and the second opening providing an outlet for the aqueous algae slurry; and
   a cathode, an anode, and an insulator forming at least a portion of the channel that defines the fluid flow path, the cathode and the anode being spaced apart to form a gap with a distance in a range from 0.5 mm to 100 mm, wherein a volume of the fluid flow path within the gap is at least 50 ml.

12. An apparatus as in claim 11, wherein the distance across the gap is in a range from 1 mm to 50 mm.

13. An apparatus as in claim 11 or claim 12, wherein the volume of the fluid flow path within the gap is at least 200 ml.

14. An apparatus as in claim 11 or claim 12, wherein a surface area of the channel formed by the cathode and the anode is in a range from at least 500 $cm^2$ to at least 2000 $cm^2$.

15. An apparatus as in claim 11 or claim 12, wherein the body comprises a first conductive tube within a second conductive tube and the insulator provides separation between the first and second conductive tubes, the channel being formed from spacing between the first and second conductive tubes.

16. An apparatus as in claim 15, further comprising rifling that creates a spiraling flow of fluid within the channel.

17. An apparatus as in claim 16, wherein the rifling is provided by the insulator.

18. An apparatus as in claim 11 or claim 12, further comprising a power supply configured to supply at least 1 amp.

* * * * *